(12) United States Patent
Goto et al.

(10) Patent No.: US 8,440,713 B2
(45) Date of Patent: May 14, 2013

(54) [1]BENZOTHIENO[3,2-B][1]BENZOTHIOPHENE COMPOUND AND METHOD FOR PRODUCING THE SAME, AND ORGANIC ELECTRONIC DEVICE USING THE SAME

(75) Inventors: Daisuke Goto, Kanagawa (JP); Masafumi Torii, Kanagawa (JP); Tamotsu Horiuchi, Shizuoka (JP); Tamotsu Aruga, Kanagawa (JP); Hiroshi Ikuno, Kanagawa (JP); Toshiya Sagisaka, Kanagawa (JP); Satoshi Yamamoto, Kanagawa (JP); Takeshi Orito, Kanagawa (JP); Masataka Mohri, Kanagawa (JP); Takashi Okada, Kanagawa (JP); Takuji Kato, Fukuoka (JP); Shinji Matsumoto, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 189 days.

(21) Appl. No.: 12/988,387

(22) PCT Filed: Apr. 15, 2009

(86) PCT No.: PCT/JP2009/057947
§ 371 (c)(1),
(2), (4) Date: Oct. 18, 2010

(87) PCT Pub. No.: WO2009/128559
PCT Pub. Date: Oct. 22, 2009

(65) Prior Publication Data
US 2011/0040107 A1    Feb. 17, 2011

(30) Foreign Application Priority Data

Apr. 17, 2008  (JP) ................................. 2008-107581
Mar. 13, 2009  (JP) ................................. 2009-061749

(51) Int. Cl.
*A61K 31/381* (2006.01)
*C07D 333/52* (2006.01)

(52) U.S. Cl.
USPC ............................................ 514/443; 549/42

(58) Field of Classification Search .................. 514/443; 549/42
See application file for complete search history.

(56) References Cited

U.S. PATENT DOCUMENTS

| | | |
|---|---|---|
| 2008/0146776 A1 | 6/2008 | Liu et al. |
| 2009/0001357 A1 | 1/2009 | Takimiya et al. |
| 2010/0032655 A1 | 2/2010 | Takimiya et al. |

FOREIGN PATENT DOCUMENTS

| | | |
|---|---|---|
| CN | 101529609 | 9/2009 |
| CN | 101563796 | 10/2009 |
| JP | 5-55568 | 3/1993 |
| JP | 2005-101493 | 4/2005 |
| JP | 2008-239987 | 10/2008 |
| JP | 2009-21389 | 1/2009 |
| JP | 2009-21390 | 1/2009 |
| JP | 2009-124064 | 6/2009 |
| TW | 200802864 A | 1/2008 |
| WO | WO 2006/077888 A1 | 7/2006 |
| WO | WO 2008/047896 A1 | 4/2008 |
| WO | WO 2008/059817 A1 | 5/2008 |
| WO | WO 2008/062841 A1 | 5/2008 |
| WO | WO 2008/069061 A1 | 6/2008 |

OTHER PUBLICATIONS

International Search Report issued Jul. 21, 2009 in Application No. PCT/JP2009/057947.
S. Y. Zherdeva, et al., Study of the possible synthesis of direct azo dyes from 2,7-diaminobenzothieno[3,2-b]benzothiophene, Izvestiya Vysshikh Uchebnykh Zavedenii, Khimiyai Khimicheskaya Tekhnologiya, 1981, vol. 24, No. 5, pp. 612-617, especially p. 615.
D. Haristoy, et al., "Structure and photoconductive behavior of a sanidic liquid crystal", Liquid Crystals, 2000, vol. 27, No. 3, pp. 321-328, especially p. 322.
S. Mery, et al., "Bipolar carrier transport in a lamello-columnar mesophase of a sanidic liquid crystal", Journal of Materials Chemistry, 2002, vol. 12, No. 1, pp. 37-41, especially Fig. 1.
B. Košata, et al., "Synthesis and mesomorphic properties of liquid crystalline [1]benzothieno[3,2-b][1]benzothiophene derivatives", Liquid Crystals, 2004, vol. 31, No. 10, pp. 1367-1380, especially compound 2.

(Continued)

*Primary Examiner* — Taofiq A Solola
(74) *Attorney, Agent, or Firm* — Oblon, Spivak, McClelland, Maier & Neustadt, L.L.P.

(57) ABSTRACT

A [1]benzothieno[3,2-b][1]benzothiophene compound expressed by General Formula (I): General Formula (I) where X and Y are each independently a hydrogen atom; a halogen atom; or a functional group having a straight or branched aliphatic alkyl group optionally having a halogen atom, a functional group having an alicyclic alkyl group optionally having a halogen atom, a functional group having a straight or branched aliphatic alkenyl group optionally having a halogen atom, a functional group having an alicyclic alkenyl group optionally having a halogen atom, a functional group having a carboxyl group, or a functional group having a thiol group, as a partial structure; and X and Y are the same or each independently different, provided that at least one of X and Y has a straight or branched aliphatic alkenyl group, an alicyclic alkenyl group, a carboxyl group or a thiol group, as a partial structure.

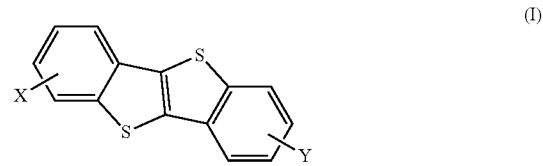

(I)

6 Claims, 6 Drawing Sheets

OTHER PUBLICATIONS

Myoung-Chul Um, et al., "High-performance organic semiconductors for thin-film transistors based on 2,7-divinyl[1]benzothieno[3,2-b]benzothiophene", Journal of Materials Chemistry, 2008, vol. 18, No. 39, pp. 4698-4703, especially Fig. 1.

S. Gillissen, et al., "Synthesis of a Processible High Molecular Weight Poly(thienylene vinylene). Polymerisation and Thin-Film Transistor Properties", Synthetic Metals, 2003, vol. 135-136, pp. 255-256.

Amanda R. Murphy, et al., "Self-Assembly, Molecular Ordering, and Charge Mobility in Solution-Processed Ultrathin Oligothiophene Films", Chemistry of Materials, 2005, vol. 17, No. 24, pp. 6033-6041.

Dean M. Delongchamp, et al., "Correlating Molecular Design to Microstructure in Thermally Convertible Oligothiophenes: The Effect of Branched versus Linear End Groups", Journal of Physical Chemistry B, 2006, vol. 110, No. 22, pp. 10645-10650.

S. F. Nelson, et al., "Temperature-independent transport in high-mobility pentacene transistors", Applied Physics Letters, vol. 72, No. 15, Apr. 13, 1998, pp. 1854-1856.

Kazuo Takimiya, et al., "2,7-Diphenyl[1]benzothieno[3,2-b]benzothiophene, A New Organic Semiconductor for Air-Stable Organic Field-Effect Transistors with Mobilities up to 2.0 $cm^2 V^{-1} s^{-1}$", J. Am. Chem. Soc., vol. 128, 2006, pp. 12604-12605.

Hideaki Ebata, et al., "Highly Soluble [1]Benzothieno[3,2-b]benzothiophene (BTBT) Derivatives for High-Performance, Solution-Processed Organic Field-Effect Transistors", J. Am. Chem. Soc., vol. 129, 2007. pp. 15732-15733.

A. R. Brown, et al., "Logic Gates Made from Polymer Transistors and Their Use in Ring Oscillators", Science, vol. 270, 1995, pp. 972-974.

M. Matters, et al., "Organic field-effect transistors and all-polymer integrated circuits", Optical Materials 12, 1999, pp. 189-197.

A. R. Brown, et al., "Precursor route pentacene metal-insulator-semiconductor field-effect transistors", J. Appl. Phys. vol. 79, No. 4, 1996, pp. 2136-2138.

Patrick B. Shea, et al., "Solution-processed nickel tetrabenzoporphyrin thin-film transistors", J. Appl. Phys., vol. 100, 2006, pp. 034502-1-034502-7.

Shinji Aramaki, et al., "Solution-processible organic semiconductor for transistor applications: Tetrabenzoporphyrin", Appl. Phys., vol. 84, No. 12, pp. 2085-2087, (2004).

The Extended European Serach Report issued Aug. 28, 2012, in Application No. / Patent No. 09731898.4-1235 / 2265619 PCT/JP2009057947.

Taiwanese Office Action issued Aug. 22, 2012, in Taiwan Patent Application No. 98112852 (with English translation).

Office Action issued Dec. 19, 2012, in Chinese patent application No. 200980113662.7 (w/English translation of Examiner Comments).

[1]BENZOTHIENO[3,2-B][1]BENZOTHIOPHENE COMPOUND AND METHOD FOR PRODUCING THE SAME, AND ORGANIC ELECTRONIC DEVICE USING THE SAME

TECHNICAL FIELD

The present invention relates to a [1]benzothieno[3,2-b][1]benzothiophene compound which can be easily produced from a [1]benzothieno[3,2-b][1]benzothiophene compound precursor having a leavable soluble group, a method for producing the compound, and an organic electronic device using the compound. A compound of the present invention is useful as a material for various organic electronics elements, such as photoelectric conversion elements, thin-film transistor elements, light-emitting elements and the like.

BACKGROUND ART

In recent years, organic thin-film transistors using organic semiconductor materials have been actively studied and developed. The organic semiconductor materials can be easily formed into a thin film by an easy process such as a wet process, for example, printing, spin coating or the like. The thin-film transistors using organic semiconductor materials also have an advantage over thin-film transistors using inorganic semiconductor materials in that the temperature of the production process can be lowered. Thus, a film can be deposited on a plastic substrate generally having a low thermal durability, so that electronic devices such as display devices can be reduced in weight and cost. Further, the electronic devices are expected to be widely used by taking advantage of flexibility of the plastic substrate.

So far, acene based materials, such as pentacene, have been reported as an organic semiconductor material of a low molecular compound (For example, Patent Literature 1 and Non-Patent Literature 1). It has been reported that an organic thin-film transistor using pentacene for an organic semiconductor layer have a relatively high field effect mobility. However, acene based materials have an extremely low solubility in a general solvent. Therefore, when such acene based material is used to form a thin organic semiconductor layer of an organic thin-film transistor, a vacuum deposition step is necessary to be performed. That is, the thin film cannot be deposited by an easy process, such as coating, printing or the like, and the acene based material does not always satisfy the expectation on the organic semiconductor material.

As one of the acene based materials similar to pentacene, 2,7-diphenyl[1]benzothieno[3,2-b][1]benzothiophene, which is a derivative of [1]benzothieno[3,2-b]benzothiophene, having a structure of the following Formula (1) (Patent Literature 2 and Non-Patent Literature 2) is deposited on a substrate treated with octadecyltrichlorosilane, so as to exhibit a mobility comparable to that of pentacene (approximately 2.0 cm$^2$/V·s) and to have prolonged stability in an atmosphere.

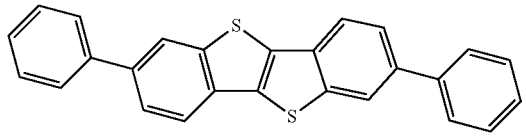

Formula (1)

Moreover, 2,7-dialkyl[1]benzothieno[3,2-b][1]benzothiophene, which is also a derivative, having a structure of the following Formula (2) (Non-Patent Literature 3) has a liquid crystal phase and high solubility, and can be applied by spin coating or casting. It is heat-treated at a relatively low temperature so as to exhibit a mobility comparable to that of pentacene (approximately 2.0 cm$^2$/V·s).

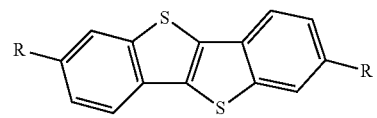

Formula (2)

However, 2,7-diphenyl[1]benzothieno[3,2-b][1]benzothiophene is necessary to be subjected to a vacuum deposition step similar to pentacene, and does not respond to the expectations to the organic semiconductor materials, namely, the expectation to realize an organic semiconductor material which can deposit a thin film by an easy process, such as coating, printing or the like. On the other hand, 2,7-dialkyl[1]benzothieno[3,2-b][1]benzothiophene has a relatively low transition temperature to a liquid crystal phase, approximately 100° C., and a configuration of a film formed from 2,7-dialkyl[1]benzothieno[3,2-b][1]benzothiophene may be changed by heat treatment after film deposition. Thus, there is a problem with process adaptability in production of an organic semiconductor device using such compound.

In recent years, a method of producing a field-effect transistor is reported, wherein a low molecular compound having high solvent solubility is used as a semiconductor precursor (hereinafter referred to as precursor), dissolved in a solvent and the like, and applied so as to deposit a film by a coating process, and then the film is transformed to a semiconductor, i.e., an organic semiconductor film, thereby forming a field-effect transistor. Examples of the methods include those using pentacene and similar aromatic hydrocarbon (Non-Patent Literatures 5 and 6), and those using porphyrin (for example, Non-Patent Literatures 7 and 8).

In those examples, a tetrachlorobenzene molecule detaches from a pentacene precursor, but tetrachlorobenzene has a high boiling point, and is hard to be removed from the reaction system. Additionally its toxicity is concerned.

Moreover, any of these examples has problems that semiconductor molecules which have been transformed are not stable to oxygen or water, thereby difficult to handle in an atmosphere.

From those reasons, the foregoing conventionally known compounds and precursors thereof clearly have problems with process adaptability, and a novel precursor and a method for producing the precursor have been demanded.

Patent Literature 1: Japanese Patent Application Laid-Open (JP-A) No. 05-055568
Patent Literature 2: International Publication No. WO 2006/077888
Non-Patent Literature 1: Appl. Phys. Lett. 72, p. 1854 (1998)
Non-Patent Literature 2: J. Am. Chem. Soc. 128, p. 12604 (2006)
Non-Patent Literature 3: J. Am. Chem. Soc. 129, p. 15732 (2007)
Non-Patent Literature 4: Science Vol. 270 (1995) p. 972
Non-Patent Literature 5: Optical Materials 12 (1999) p. 189
Non-Patent Literature 6: J. Appl. Phys. 79, p. 2136 (1996)

Non-Patent Literature 7: J. Appl. Phys. 100, p. 034502 (2006)

Non-Patent Literature 8: Appl. Phys. Lett. 84, 12, p. 2085 (2004)

DISCLOSURE OF INVENTION

The present invention has been made in view of the current situation of the related art, and aimed to provide a novel precursor having a [1]benzothieno[3,2-b][1]benzothiophene skeleton, which is excellent in carrier mobility (field-effect mobility), solubility, and oxidation stability, and having high solubility and desirable film deposition properties, to provide a novel compound which can be easily formed from the precursor by application of energy, and a method for producing the compound. The compound is useful for application to organic electronic devices, particularly organic thin-film transistors.

Means for solving the above-described problems are described below.

<1> A [1]benzothieno[3,2-b][1]benzothiophene compound expressed by General Formula (I):

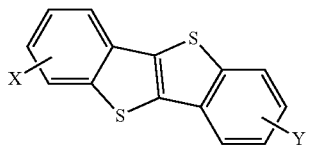

General Formula (I)

where X and Y are each independently a hydrogen atom; a halogen atom; or a functional group having a straight or branched aliphatic alkyl group optionally having a halogen atom, a functional group having an alicyclic alkyl group optionally having a halogen atom, a functional group having a straight or branched aliphatic alkenyl group optionally having a halogen atom, a functional group having an alicyclic alkenyl group optionally having a halogen atom, a functional group having a carboxyl group, or a functional group having a thiol group, as a partial structure; and X and Y are the same or each independently different, provided that at least one of X and Y has a group selected from the group consisting of a straight or branched aliphatic alkenyl group, an alicyclic alkenyl group, a carboxyl group and a thiol group, as a partial structure.

<2> The [1]benzothieno[3,2-b][1]benzothiophene compound according to <1>, wherein the functional group having a straight or branched aliphatic alkenyl group or an alicyclic alkenyl group, the functional group having a carboxyl group and the functional group having a thiol group respectively have structures expressed by General Formulas (II) to (IV):

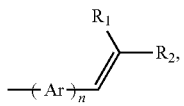

General Formula (II)

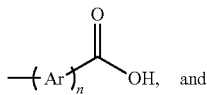

General Formula (III)

General Formula (IV)

in General Formulas (II) to (IV), Ar is a divalent functional group, n is an integer of 0 or more, when n is 2 or more, Ars are the same or each independently different, $R_1$ and $R_2$ are each independently a hydrogen atom, a straight or branched aliphatic alkyl group optionally having a halogen atom, or an alicyclic alkyl group optionally having a halogen atom.

<3> The [1]benzothieno[3,2-b][1]benzothiophene compound according to <2>, wherein Ar is selected from the group consisting of benzene, thiophene, naphthalene and thienothiophene, each of which optionally has a substituent, in General Formulas (II) to (IV).

<4> The [1]benzothieno[3,2-b][1]benzothiophene compound according to any one of <2> and <3>, wherein n is 0 to 2.

<5> A method for producing a [1]benzothieno[3,2-b][1]benzothiophene compound, including:

transforming a [1]benzothieno[3,2-b][1]benzothiophene compound precursor having a leaving group into the [1]benzothieno[3,2-b][1]benzothiophene compound as defined in any one of <1> to <4>.

<6> The method for producing a [1]benzothieno[3,2-b][1] benzothiophene compound according to <5>, wherein the leaving group is a group having one of partial structures expressed by General Formulas (V) to (VII):

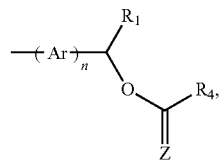

General Formula (V)

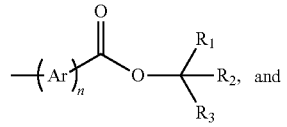

General Formula (VI)

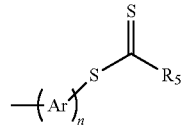

General Formula (VII)

In General Formulas (V) to (VII), n is an integer of 0 or more, Ar is a divalent group optionally having a substituent, when n is an integer of 2 or more, Ars are the same or each independently different, Z is an oxygen atom or a sulfur atom, $R_1$, $R_2$ and $R_3$ are each independently a hydrogen atom, a straight or branched aliphatic alkyl group optionally having a halogen atom or an alicyclic alkyl group optionally having a halogen atom, $R_4$ is a hydrogen atom, an aliphatic alkyl group having 1 or more carbon atoms and optionally having a halogen atom, an alicyclic alkyl group having 1 or more carbon atoms and optionally having a halogen atom, and a straight or branched alkoxyl group having 1 or more carbon atoms and optionally having a halogen atom, a straight or branched thioalkoxyl group having 1 or more carbon atoms and optionally having a halogen atom, and $R_5$ is a straight or branched alkoxyl group having 1 or more carbon atoms.

<7> An organic electronic device including the [1]benzothieno[3,2-b][1]benzothiophene compound according to any one of <1> to <4>.

<8> The organic electronic device according to <7>, wherein the organic electronic device includes the [1]benzothieno[3,2-b][1]benzothiophene compound produced by the method according to any one of <5> and <6>.

<9> The organic electronic device according to any one of <7> and <8>, wherein the organic electronic device is an organic thin-film transistor.

According to the present invention, the [1]benzothieno[3,2-b]benzothiophene compound (hereinafter, referred to as a specific compound) having high carrier mobility (field-effect mobility) and oxidation stability, which can form an organic semiconductor can be provided.

The specific compound of the present invention can be easily produced from a specific compound precursor (hereinafter referred to as a precursor) having sufficient solubility to an organic solvent.

Moreover, the field-effect transistor of the present invention has advantages of high carrier mobility (field-effect mobility), high on/off ratio and low leak current.

BEST MODE FOR CARRYING OUT THE INVENTION

Figure 1:
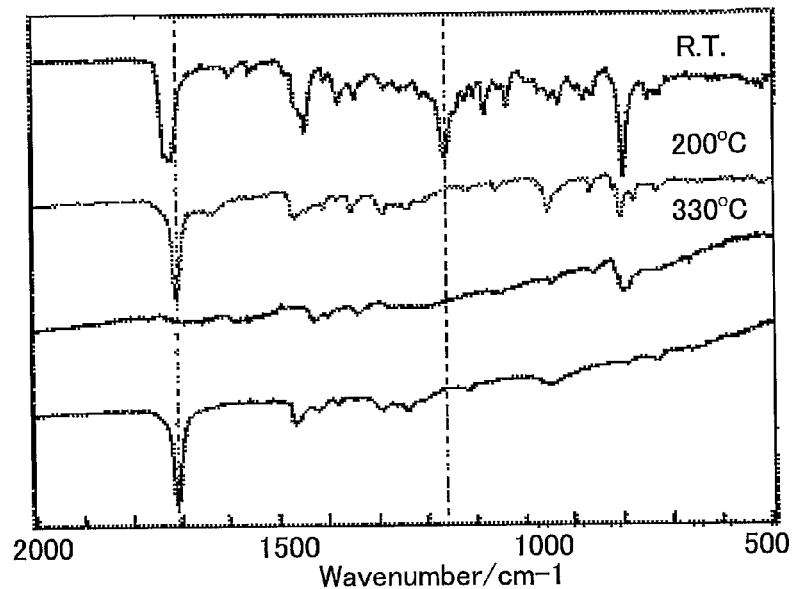
FIG. 1 shows IR spectra of Precursor 1 of the present invention (temperature variation from a room temperature to 330° C.) and an IR spectrum of a separated carboxylic acid.

Hereinafter, a specific compound of the present invention and a method for producing the specific compound, and an organic transistor using the specific compound will be specifically explained.

[1]benzothieno[3,2-b][1]benzothiophene is proposed to be used as an organic semiconductor material having excellent oxidation stability, as it has a highly-developed π conjugated system and highly planar structure, and has relatively higher ionization potential than that of other acene based materials, such as pentacene. Specifically, it is proposed in Non-Patent Literatures 3 and 4. However, when [1]benzothieno[3,2-b][1]benzothiophene does not have a soluble substituent, high vacuum is necessary for film deposition. When [1]benzothieno[3,2-b][1]benzothiophene is substituted with a soluble group such as an aliphatic alkyl group, it can relatively obtain solubility, but it often has a plurality of phase transition points at low temperatures, causing a failure to form a desired film configuration by heat treatment upon device production or the like. Thus, the inventors of the present invention have been found that the above problems can be solved by use of the precursor having a leaving group having high solubility, which can be easily formed into the specific compound including an alkenyl group, thiol group and/or carboxyl group as a partial structure, by application of energy.

A soluble leaving group is added to a precursor so as to ensure solubility to an organic solvent, and an external stimulus such as heat, light or the like is applied to the precursor after film deposition so as to transform the precursor into a molecule having an alkenyl group, thiol group and/or carboxyl group as a partial structure, thereby leading to a high crystallinity structure. Thus, crystallization can be accelerated. As a result, the accelerated crystallization state enables to obtain higher mobility than an amorphous state or microcrystalline state of the precursor.

A compound of the present invention expressed by General Formula (I) having a structure expressed by General Formulas (II) to (VII) and the like may be produced by conventionally known various coupling reactions. Examples thereof include Suzuki coupling reaction, Stille coupling reaction, Kumada coupling reaction, Negishi coupling reaction, Hiyama coupling reaction, Sonogashira reaction, Heck reaction and Wittig reaction. Of these, Suzuki coupling reaction and Stille coupling reaction are particularly preferred in terms of easy derivatization of an intermediate, reactivity and yield.

Synthesis examples of [1]benzothieno[3,2-b][1]benzothiophene compound of the present invention by the Suzuki coupling reaction and Stille coupling reaction are described as follows.

In the case of Suzuki coupling reaction, a [1]benzothieno[3,2-b][1]benzothiophene derivative, i.e. 2,7-halogenated[1]benzothieno[3,2-b][1]benzothiophene expressed by General Formula (VIII), a boronic acid derivative, expressed by General Formula (IX) and base are added and reacted in the presence of palladium catalyst so as to produce the [1]benzothieno[3,2-b][1]benzothiophene compound of the present invention.

In the case of Stille coupling reaction, a [1]benzothieno[3,2-b][1]benzothiophene derivative, i.e. 2,7-halogenated[1]benzothieno[3,2-b][1]benzothiophene, expressed by General Formula (VIII) and an organotin derivative expressed by General Formula (IX) are added and reacted in the presence of palladium catalyst so as to produce the [1]benzothieno[3,2-b][1]benzothiophene compound of the present invention.

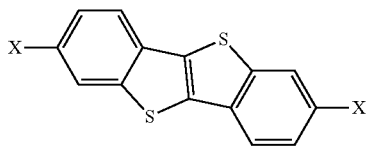

General Formula (VIII)

In General Formula (VIII), X represents a chlorine atom, bromine atom, or iodine atom.

Y—Ar

General Formula (IX)

In General Formula (IX), Ar represents a divalent group which may have a substituent; Y represents boronic acid or ester thereof, or an organotin functional group.

In the synthesis methods by the Suzuki coupling reaction or Stille coupling reaction, a halogen atom in the halogenated [1]benzothieno[3,2-b][1]benzothiophene derivative expressed by General Formula (VIII) is not particularly limited. It is preferably an iodine atom or bromine atom in terms of reactivity.

As the organotin derivative expressed by General Formula (IX), a derivative having a trialkyl tin group such as $SnMe_3$ group or $SnBu_3$ group may be used. As the boronic acid derivative expressed by General Formula (IX), arylboronic acid may be used, and additionally boronate ester may be used, which is synthesized from a halogenated derivative using bis(pinacolato)diboron which is thermally stabile and can be easily handed in air.

For the Stille coupling reaction base is not necessary, while for the Suzuki coupling reaction base is necessary, and a relatively weak base, such as $Na_2CO_3$, or $NaHCO_3$ contributes to a good result. In the case where steric hindrance effects on the reaction, a strong base such as $Ba(OH)_2$, $K_3PO_4$ or NaOH is effective.

Additionally, caustic potash and metal alkoxides, such as potassium t-butoxide, sodium t-butoxide, lithium t-butoxide, potassium 2-methyl-2-butoxide, sodium 2-methyl-2-butoxide, sodium methoxide, sodium ethoxide, potassium ethoxide and potassium methoxide may be also used as the bases. Moreover, organic bases such as triethylamine may be also used.

Examples of the palladium catalysts include palladium bromide, palladium chloride, palladium iodide, palladium cyanide, palladium acetate, palladium trifluoroacetate, palladium acetyl acetonato [Pd(acac)$_2$], diacetate bis(triphenylphosphine)palladium [Pd(OAc)$_2$(PPh$_3$)$_2$], tetrakis(triphenylphosphine)palladium[Pd(PPh$_3$)$_4$], dichloro bis(acetonitrile)palladium[Pd(CH$_3$CN)$_2$Cl$_2$], dichloro bis(benzonitrile)palladium[Pd(PhCN)$_2$Cl$_2$], dichloro[1,2-bis(diphenylphosphino)ethane]palladium[Pd(dppe)Cl$_2$], dichloro[1,1-bis(diphenylphosphino)ferrocene]palladium [Pd(dppf)Cl$_2$], dichloro bis(tricyclohexylphosphine)palladium[Pd[P(C$_6$H$_{11}$)$_3$]$_2$Cl$_2$], dichloro bis(triphenylphosphine)palladium[Pd(PPh$_3$)$_2$Cl$_2$], tris (dibenzylideneacetone) dipalladium[Pd$_2$(dba)$_3$], and bis(dibenzylideneacetone) palladium[Pd(dba)$_2$]. Of these, phosphine catalysts such as tetrakis(triphenylphosphine)palladium[Pd(PPh$_3$)$_4$], dichloro [1,2-bis(diphenylphosphino)ethane]palladium[Pd(dppe) Cl$_2$], dichloro bis(triphenylphosphine)palladium[Pd (PPh$_3$)$_2$Cl$_2$] are preferred.

In addition to the above-described palladium catalysts, a palladium catalyst synthesized by reaction of a palladium complex and a ligand in a reaction system can be also used. Example of the ligands include triphenylphosphine, trimethylphosphine, triethylphosphine, tris(n-butyl)phosphine, tris (tert-butyl)phosphine, bis(tert-butyl)methylphosphine, tris(i-propyl)phosphine, tricyclohexylphosphine, tris(o-tolyl) phosphine, tris(2-furyl)phosphine, 2-dicyclohexylphosphinobiphenyl, 2-dicyclohexylphosphino-2'-methylbiphenyl, 2-dicyclohexylphosphino-2',4',6'-triisopropyl-1,1'-biphenyl, 2-dicyclohexylphosphino-2',6'-dimethoxy-1,1'-biphenyl, 2-dicyclohexylphosphino-2'-(N, N'-dimethylamino)biphenyl, 2-diphenylphosphino-2'-(N,N'-dimethylamino)biphenyl, 2-(di-tert-butyl)phosphine-2'-(N, N'-dimethylamino)biphenyl, 2-(di-tert-butyl) phosphinobiphenyl, 2-(di-tert-butyl)phosphino-2'-methylbiphenyl, diphenylphosphino ethane, diphenylphosphino propane, diphenylphosphino butane, diphenylphosphino ethylene, diphenylphosphino ferrocene, ethylenediamine, N,N',N'',N'''-tetramethylethylenediamine, 2,2'-bipyridyl, 1,3-diphenyldihydro imidazolylidene, 1,3-dimethyl dihydroimidazolylidene, diethyl dihydroimidazolylidene, 1,3-bis(2,4,6-trimethylphenyl)dihydroimidazolylidene and 1,3-bis(2,6-diisopropylphenyl) dihydroimidazolylidene. A palladium catalyst in which any of these ligands coordinates can be used as a cross coupling catalyst.

A reaction solvent preferably has no functional group reactive with a raw material and can appropriately dissolve the raw material. Examples thereof include: water; alcohols or ethers such as methanol, ethanol, isopropanol, butanol, 2-methoxyethanol, 1,2-dimethoxyethane, bis(2-methoxyethyl)ether; cyclic ethers such as dioxane, tetrahydrofuran; benzene; toluene; xylene; chlorobenzene; dichlorobenzene; dimethyl sulfoxide (DMSO); N,N-dimethylformamide (DMF); N,N-dimethylacetamide; N-methylpyrrolidone; and 1,3-dimethyl-2-imidazolidinone. These solvents may be used alone or in combination. Moreover, it is preferred that these solvents be preliminarily dried and deaerated.

The temperature of the above-described reaction may be appropriately set depending on the reactivity of a raw material used or a reaction solvent. It is generally 0° C. to 200° C., and preferably a boiling point or lower of the solvent in any case. Additionally, the temperature is preferably set at an elimination temperature or lower of a leaving group in terms of yield. Specifically, it is preferably a room temperature to 150° C., more preferably a room temperature to 120° C., and particularly preferably 40° C. to 100° C.

The reaction time of the above reaction may be approximately set depending on the reactivity of a raw material used. It is preferably 1 hour to 72 hours, and more preferably 1 hour to 24 hours.

The thus obtained [1]benzothieno[3,2-b][1]benzothiophene compound can be used by removing impurities such as the catalyst used for reaction, unreacted raw materials, or by-products generated upon reaction such as boronic acid salts, organotin derivatives or the like. For the purification, conventionally known methods may be used, for example, reprecipitation, column chromatography, adsorption, extraction (including Soxhlet extraction), ultrafiltration, dialysis, use of scavenger for removing a catalyst, or the like.

In order to deposit a thin film from the specific compound of the present invention obtained by the above-described production method, conventionally known film deposition methods may be used, for example, spin coating, casting, dipping, inkjetting, doctor blade casting, screen printing, vacuum deposition, or sputtering. Any of these methods enables to deposit a good thin film having excellent strength, toughness, durability and the like without cracks. Moreover, an external stimulus is applied to the film of the precursor of the present invention deposited by the film deposition method, so as to eliminate a soluble substituent, thereby depositing a film of the specific compound of the present invention. The specific compound may be used as various materials for functional elements such as photoelectric conversion elements, thin-film transistor elements, light-emitting elements and the like, Specific examples of the thus obtained specific compound of the present invention and the precursor thereof will be described as follows:

Specific examples of the hydrogen atom, the straight or branched aliphatic alkyl groups optionally having a halogen atom and the alicyclic alkyl groups optionally having a halogen atom in X, Y, and $R_1$ to $R_5$ in General Formulas (I) to (VII), include a hydrogen atom, methyl group, ethyl group, n-propyl group, i-propyl group, t-butyl group, s-butyl group, n-butyl group, i-butyl group, pentyl group, hexyl group, heptyl group, octyl group, nonyl group, decyl group, undecyl group, dodecyl group, tridecyl group, tetradecyl group, pentadecane group, hexadecyl group, heptadecyl group, octadecyl group, 3,7-dimethyloctyl group, 2-ethylhexyl group, trifluoromethyl group, trifluorooctyl group, trifluorododecyl group, trifluorooctadecyl group, 2-cyanoethyl group, benzyl group, 4-chlorobenzyl group, 4-methylbenzyl group, cyclopentyl group and cyclohexyl group.

In the case where $R_4$ and $R_5$ are each independently a straight or branched alkoxyl group having 1 or more carbon atoms or a straight or branched thioalkoxyl group having 1 or more carbon atoms, in the above-exemplified functional groups, an alkoxyl group or thioalkoxyl group, in which an oxygen atom or sulfur atom is introduced in a binding position of an alkyl group having no halogen atom is exemplified.

As the straight or aliphatic alkenyl group, those having a double bond which is transformed from one or more of any carbon-carbon single bond present in an alkyl group having 2 or more carbon atoms and an aliphatic alkyl group having 2 or more carbon atoms, is exemplified. Specific examples thereof include an ethenyl group (vinyl group), propenyl group (allyl group), 1-butenyl group, 2-butenyl group, 2-methyl-2-butenyl group, 1-pentenyl group, 2-pentenyl group, 3-pentenyl group, 1-hexenyl group, 2-hexenyl group, 3-hexenyl group, 1-heptenyl group, 2-heptenyl group, 3-heptenyl group, 4-heptenyl group, 1-octenyl group, 2-octenyl group, 3-octenyl group, 4-octenyl group, 1-cycloallyl group, 1-cyclobutenyl group, 1-cyclopentenyl group, 2-cyclopentenyl group, 3-cyclopentenyl group, 1-cyclohexenyl group, 2-cyclohexenyl group, 3-cyclohexenyl group, 1-cycloheptenyl group, 2-cycloheptenyl group, 3-cycloheptenyl group and 4-cycloheptenyl group. When the alkenyl group has a trans conformation and cis conformation, either the trans conformation or cis conformation, or combinations thereof at any ratio may be used.

In the case where Ar in General Formulas (II) to (VII) represents a divalent functional group, examples of the Ars include divalent groups such as benzene, naphthalene, anthracene, pyrene, fluorene, 9,9-dimethylfluorene, azulene, triphenylene, chrysene, 9-benzylidenefluorene, $^5$H-dibenzo[a,d]cycloheptene, [2,2]-paracyclophane, triphenylamine, thiophene, thienothiophene, benzothiophene, dithienylbenzene, (fran, benzofran, carbazole) and benzodithiazole. These may have an alkyl group, alkoxy group, thioalkoxy group or halogen group as a substituent.

As the alkyl group, a straight, branched or cyclic alkyl group having 1 or more carbon atoms is used. Moreover, the alkyl group may have a phenyl group which is substituted with a halogen atom (for example, fluorine atom, chlorine atom, bromine atom, iodine atom), cyano group, phenyl group, or straight or branched alkyl group.

Specific examples of the alkyl groups include a methyl group, ethyl group, n-propyl group, i-propyl group, t-butyl group, s-butyl group, n-butyl group, i-butyl group, pentyl group, hexyl group, heptyl group, octyl group, nonyl group, decyl group, undecyl group, dodecyl group, tridecyl group, tetradecyl group, pentadecane group, hexadecyl group, heptadecyl group, octadecyl group, 3,7-dimethyloctyl group, 2-ethylhexyl group, trifluoromethyl group, trifluorooctyl group, trifluorododecyl group, trifluorooctadecyl group, 2-cyanoethyl group, benzyl group, 4-chlorobenzyl group, 4-methylbenzyl group, cyclopentyl group, and cyclohexyl group.

In the case of a substituted or unsubstituted alkoxy group or thioalkoxy group, an alkoxy group or thioalkoxy group, in which an oxygen atom or a sulfur atom is respectively introduced in a binding position of the alkyl group mentioned above, is exemplified.

Moreover, examples of the structures of the specific compounds of the present invention are as follows.

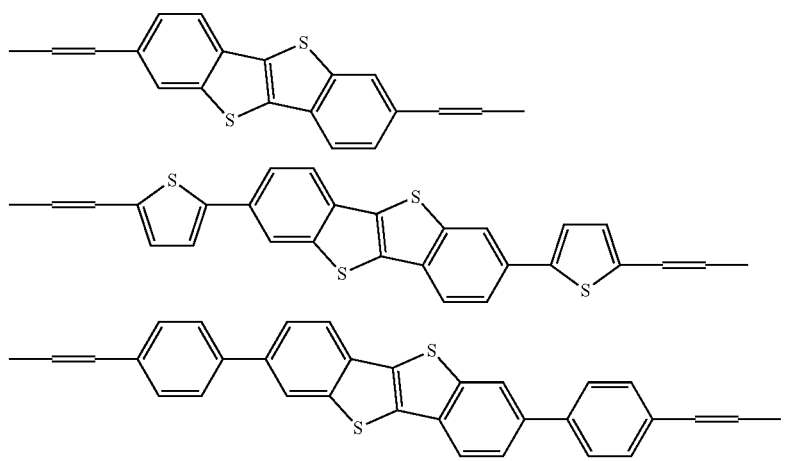

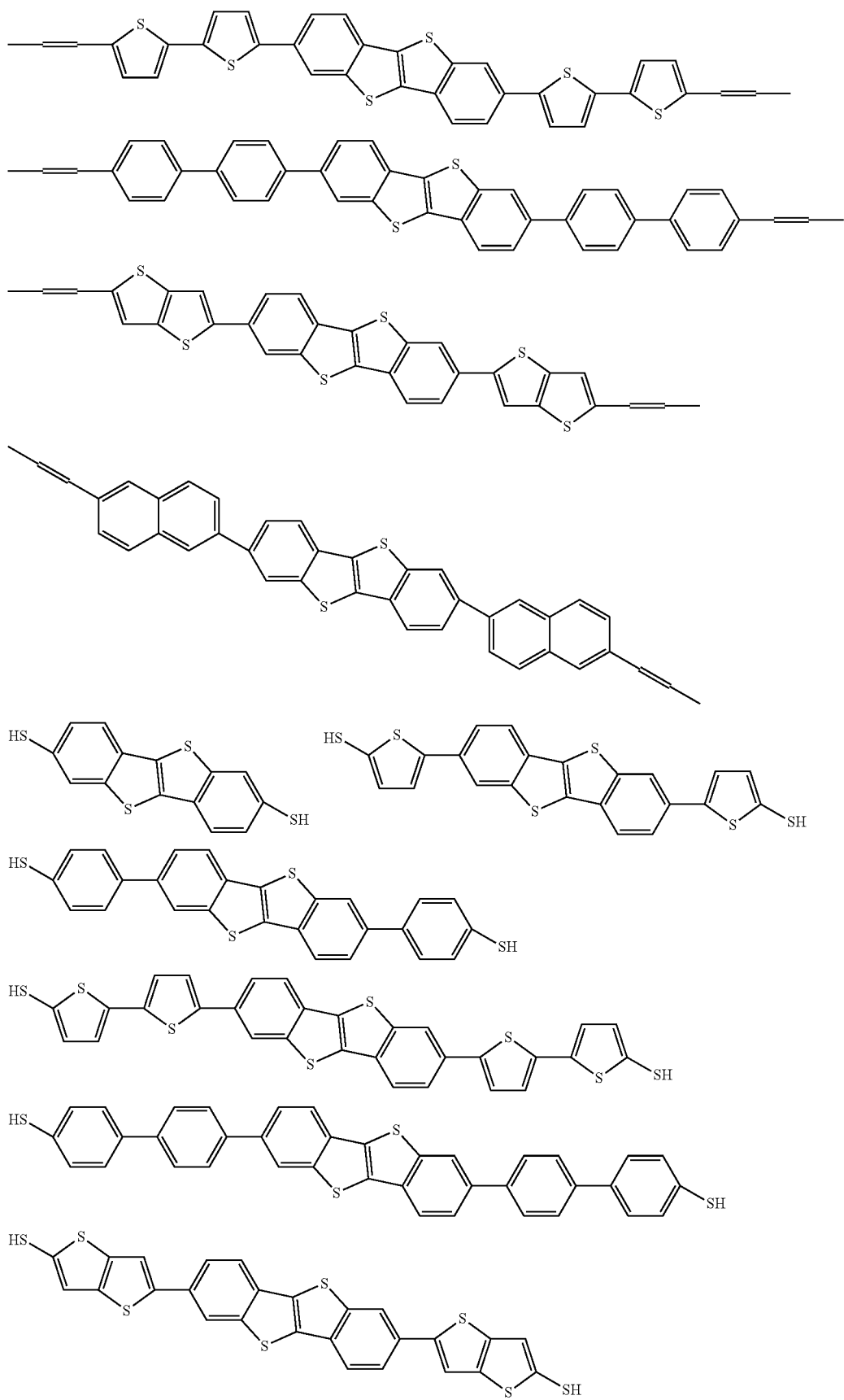

-continued
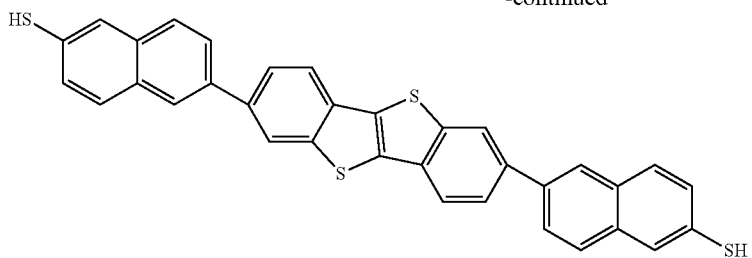
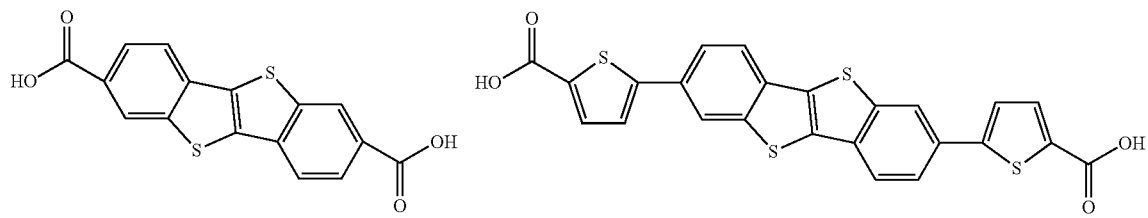
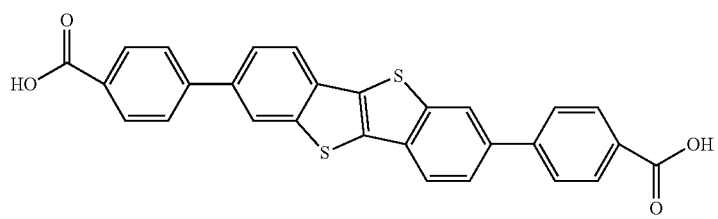
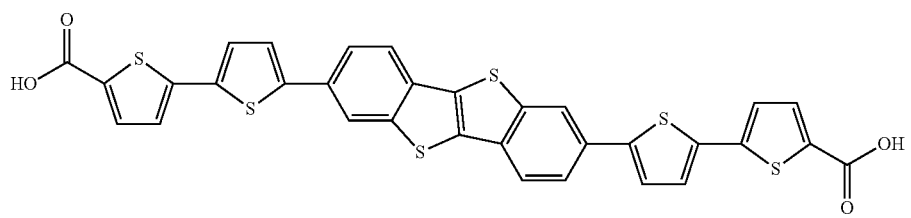
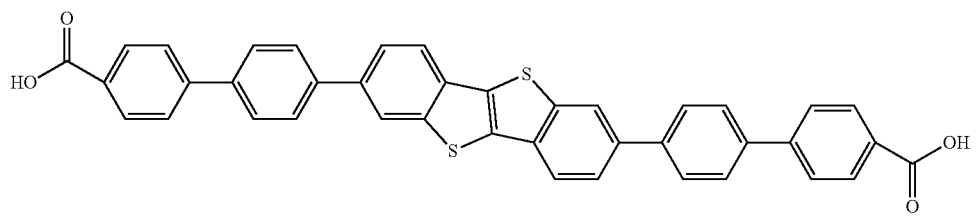
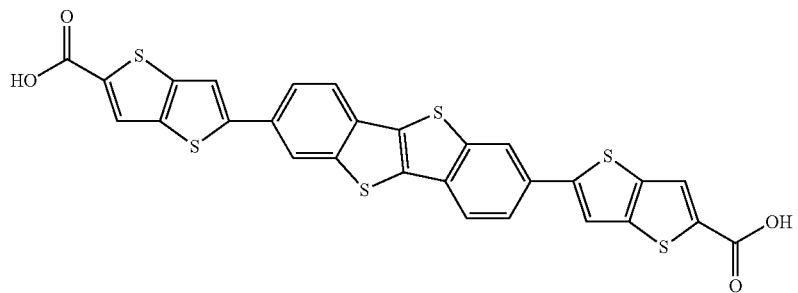

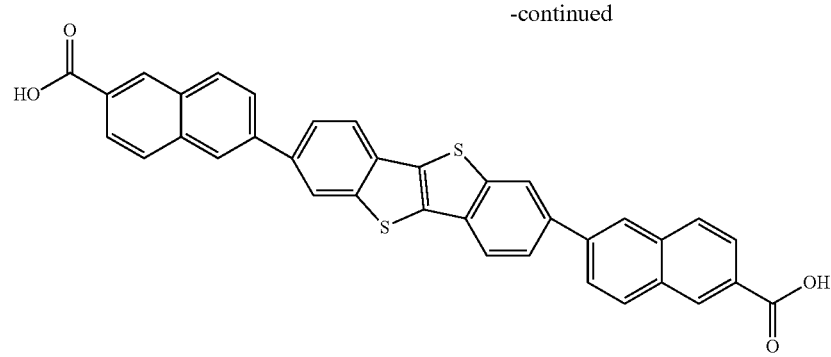
Moreover, the structures of the precursors will be specifically exemplified, but the precursor of the present invention is not limited thereto.
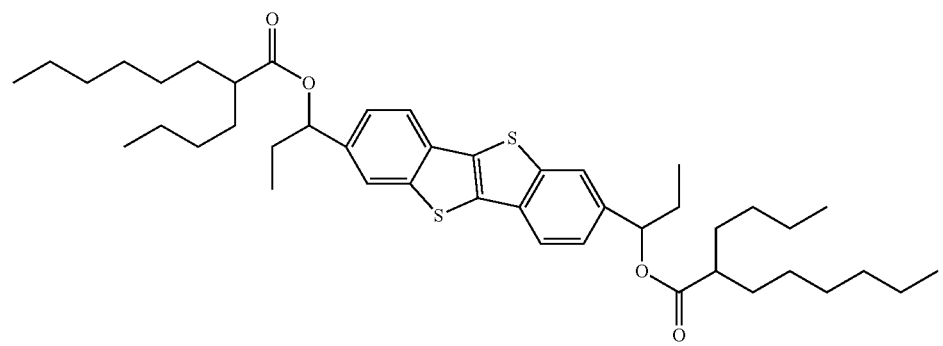
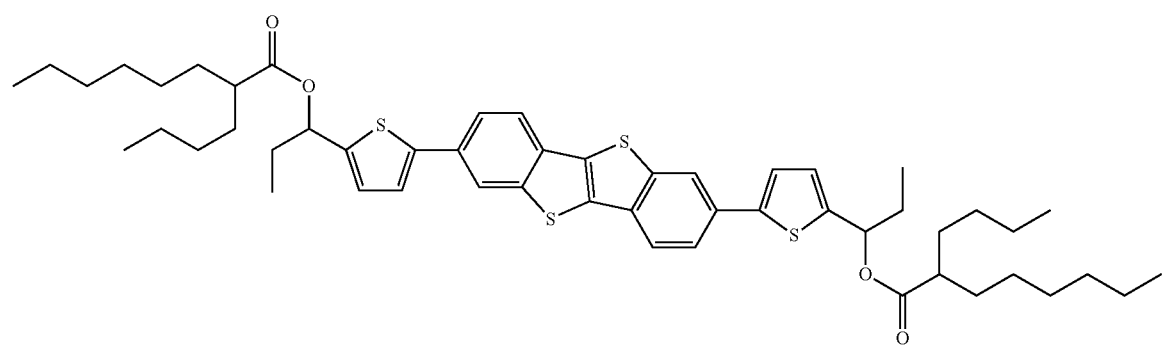
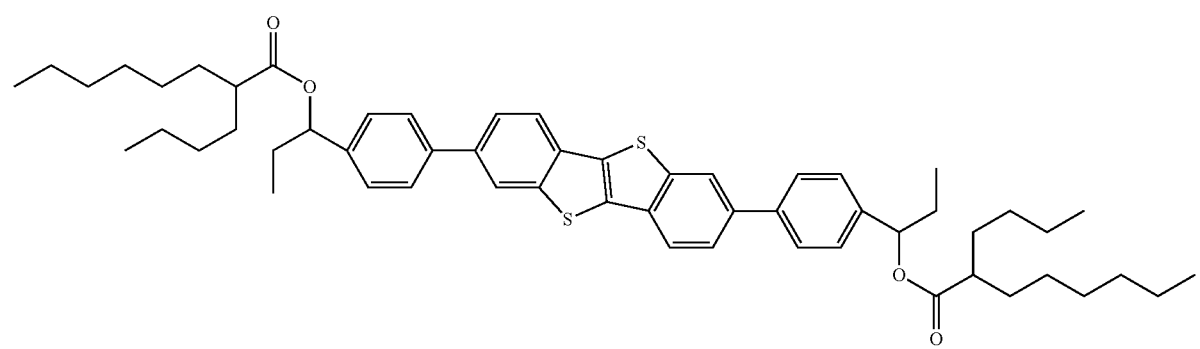

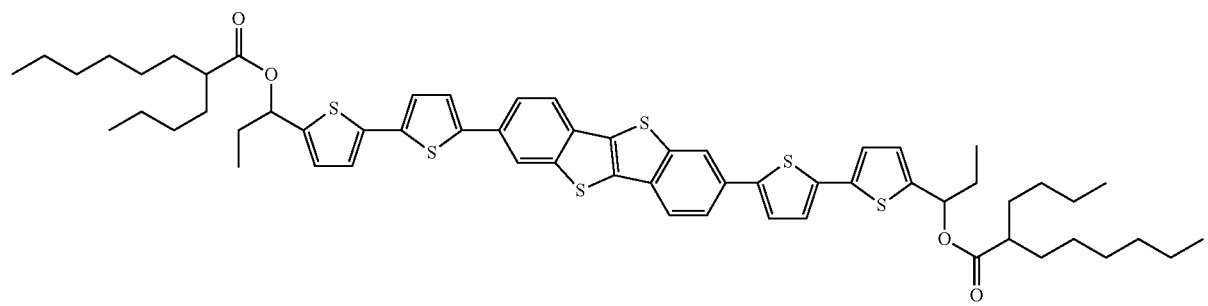
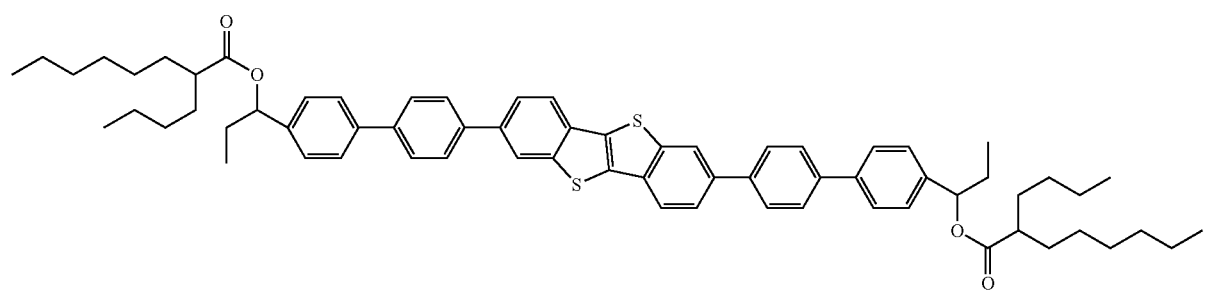
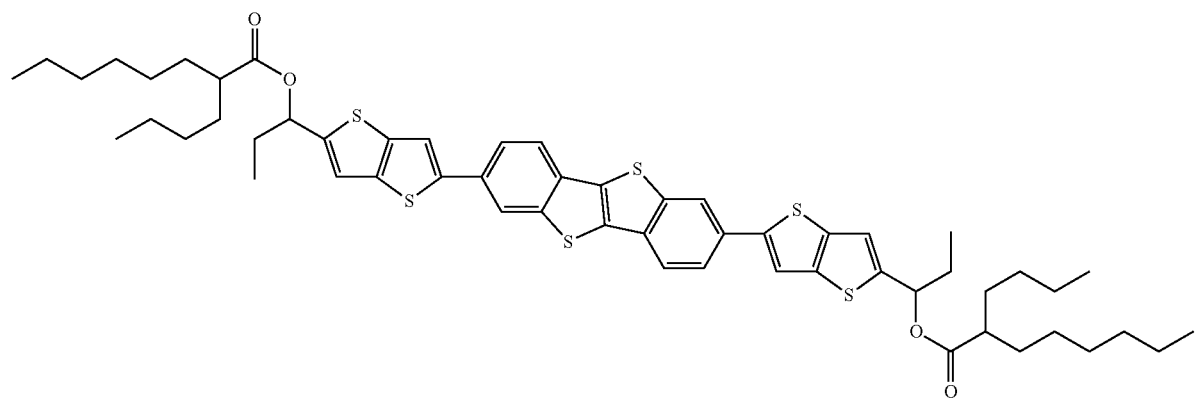
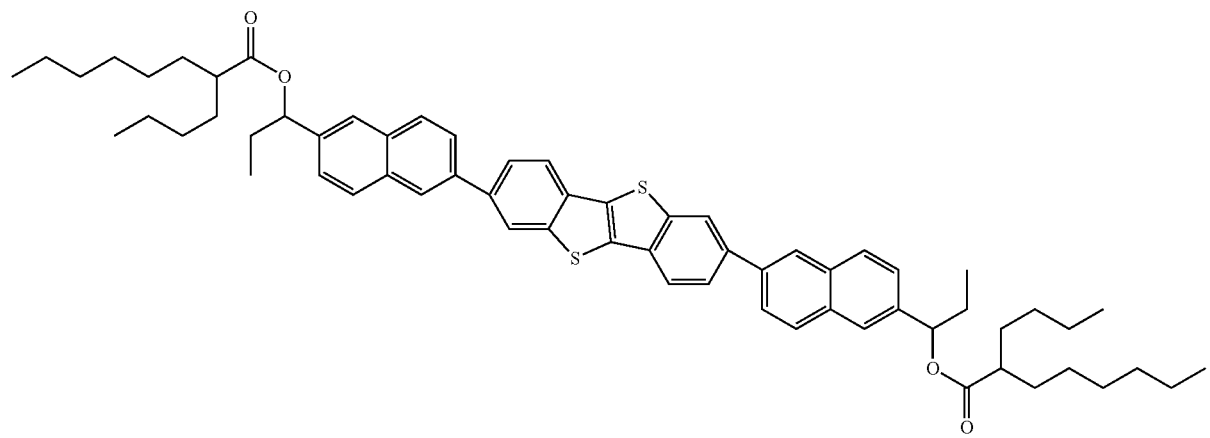

-continued
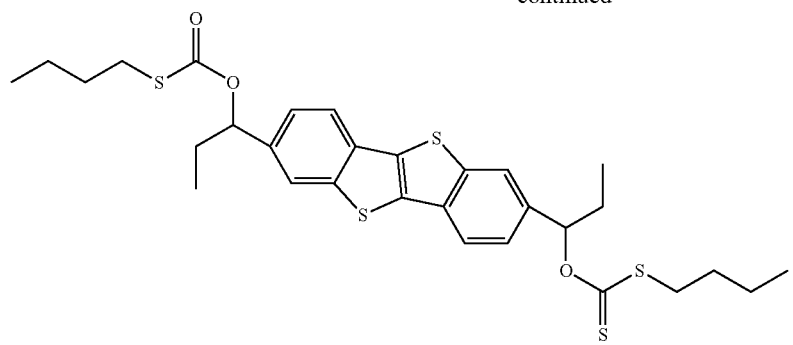
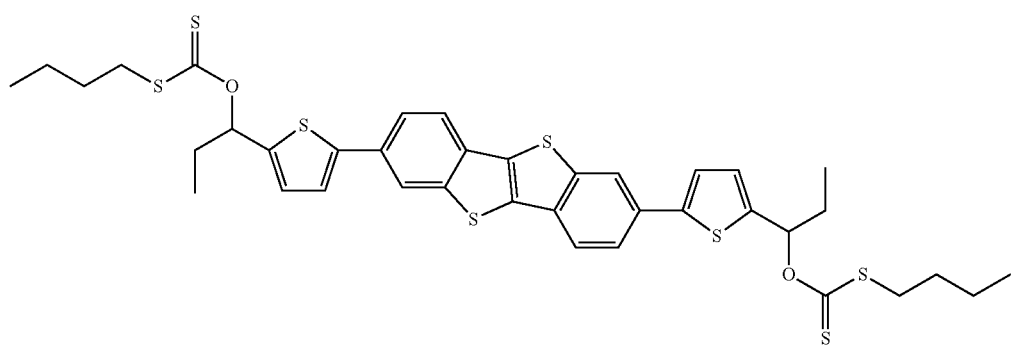
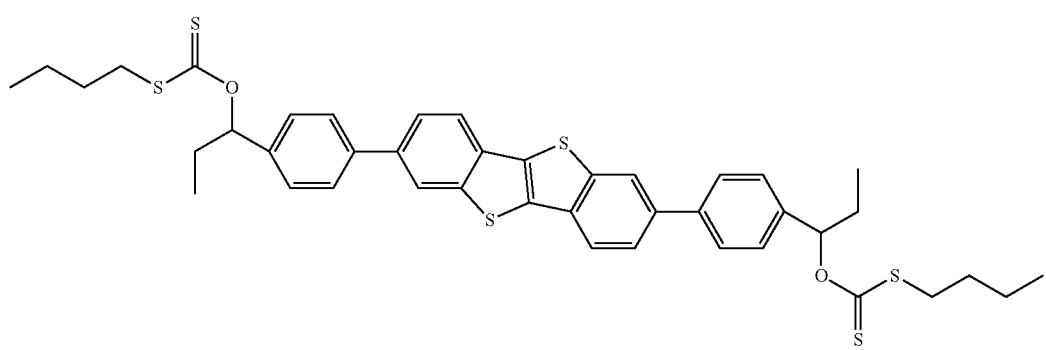
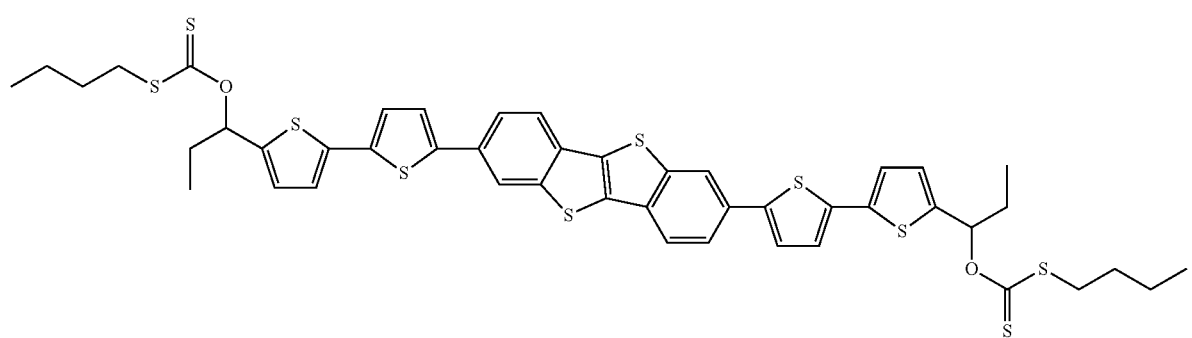
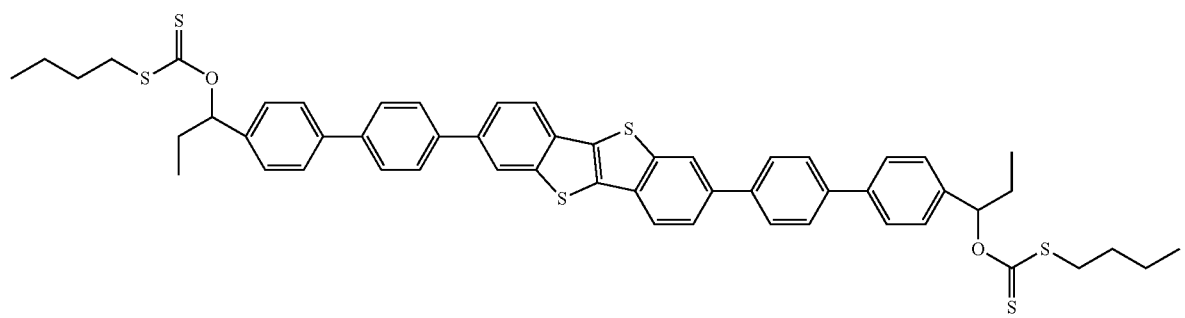

-continued
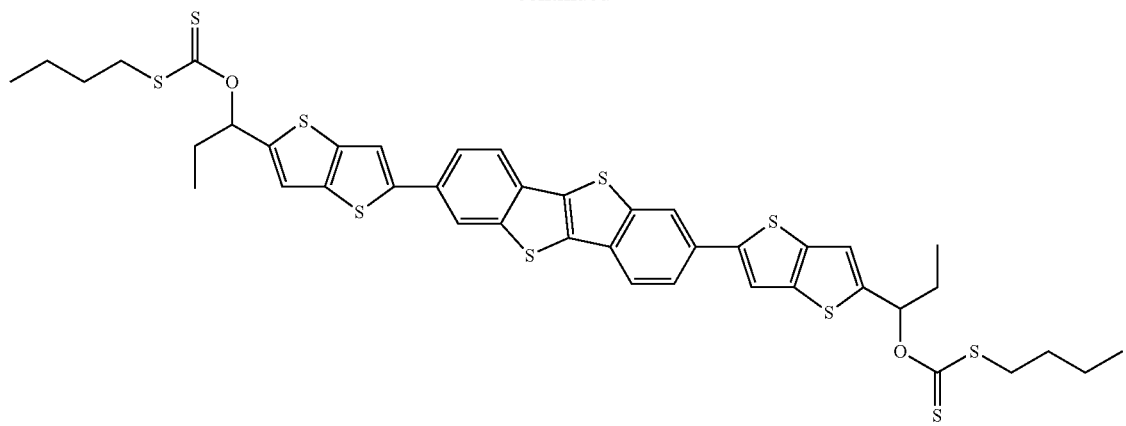
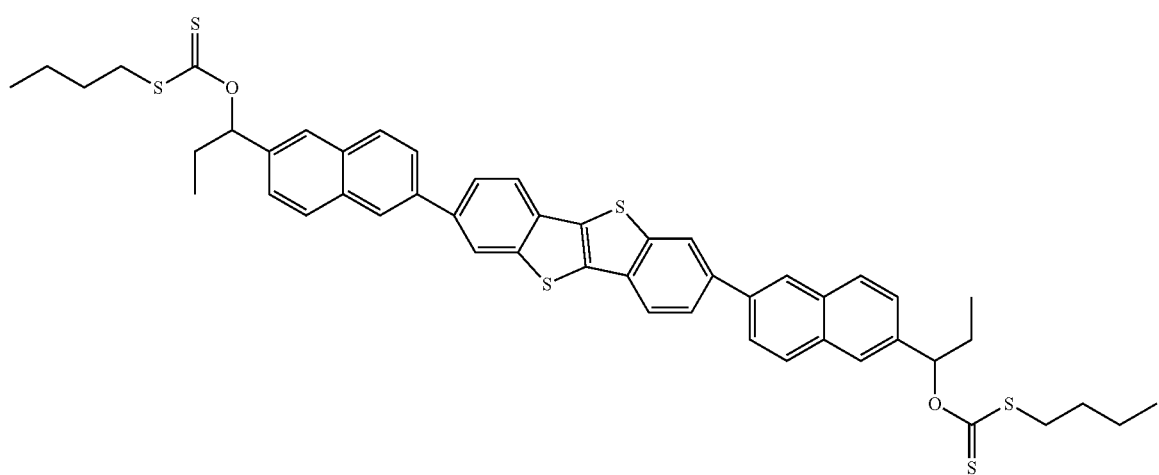
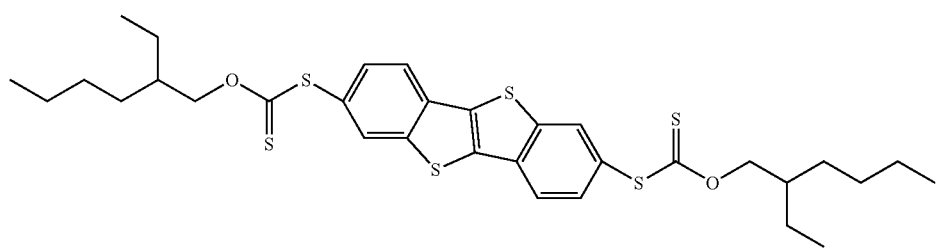
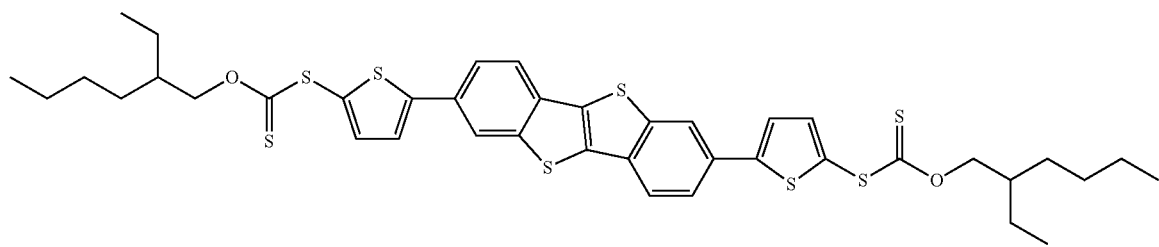
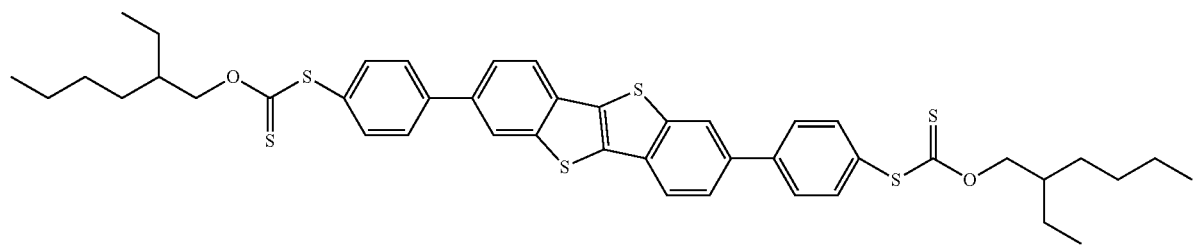

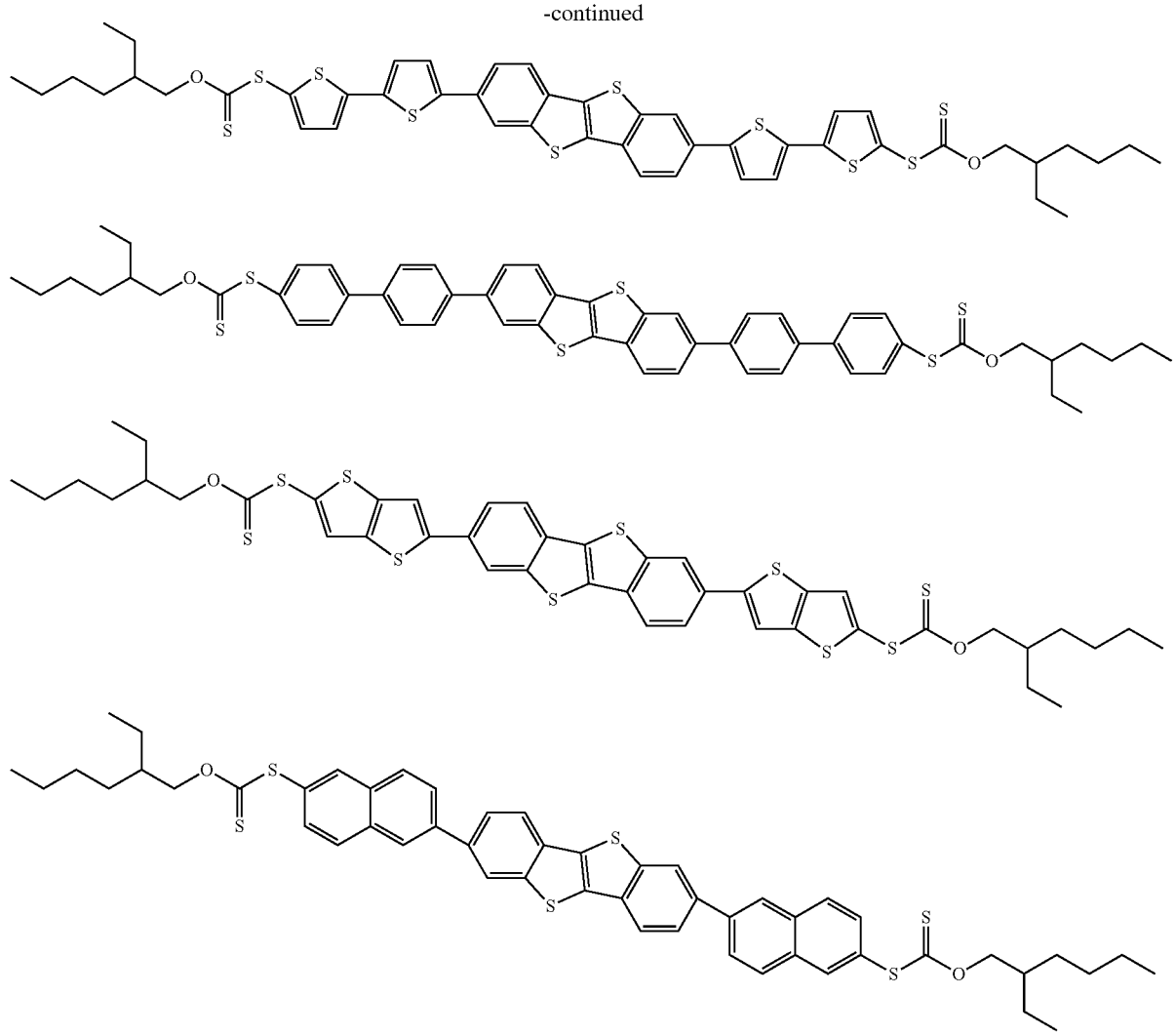

The above-exemplified precursors have a leaving group. In the specification, a leaving group means a functional group detaches from the specific compound by application of energy, to thereby changing the structure of the residual specific compound. The compound of the present invention can be obtained by applying energy to the precursor having the leaving group so as to change the structure of the precursor along with the structural change of the leaving group.

Examples of the leaving groups include, but not limited thereto, esters such as carbonate, carboxylate, xanthate, sulfonate and phosphate; and aminoxide, sulfoxide and selenoxide, each of which has β-hydrogen.

Examples of methods for forming the leaving group include, but not limited thereto, a method in which phosgene is reacted with alcohol so as to obtain carbonate, a method in which alcohol is reacted with acid chloride so as to obtain carboxylate, a method in which a base and carbon disulfide are added in alcohol, and alkyl iodide is reacted therewith to obtain xanthate, a method in which tertiary amine is reacted with hydrogen peroxide or carboxylic acid so as to obtain amine oxide, and a method in which ortho selenocyano nitrobenzene is reacted with alcohol so as to obtain selenoxide.

Examples of compounds eliminated from the precursor include, but not limited thereto, carbon dioxide, alcohols, carboxylic acids, sulfonic acids, thiols and carbonyl sulfide, and derivatives having olefin structure.

Examples of functional groups included in the compound, which is obtained by eliminating elimination components such as the above-mentioned compounds, include an alkenyl group, carboxyl group, hydroxyl group and thiol group.

Examples of the energies applied for inducing elimination reaction include heat, light and electromagnetic wave. Heat or light is preferred in terms of reactivity, yield or post treatment. Particularly preferred is heat. As the catalyst for reaction, addition of an acid and/or base is also effective. These may be directly used, or vaporized so as to perform reaction in the atmosphere.

Examples of the acids include hydrochloric acid, nitric acid, sulfuric acid, acetic acid, trifluoroacetic acid, trifluoromethanesulfonic acid, formic acid, phosphoric acid and 2-butyl octanoic acid.

Examples of the bases include, but not limited thereto, hydroxides such as sodium hydrate, potassium hydrate, carbonates such as sodium hydrogen carbonate, sodium carbonate, potassium carbonate, amines such as triethylamine and pyridine, and amidines such as 1,8-diazabicyclo[5.4.0]undec-7-ene and 1,5-diazabicyclo[4.3.0]non-5-ene.

Examples of heating methods for performing elimination reaction include, but not limited thereto, a method for heating on a support, a method for heating in an oven, a method for irradiation with microwave, a method for heating by converting light to heat using a laser beam, and a method using a photothermal conversion layer.

Heating temperature for performing elimination reaction is a room temperature to 500° C. In view of energy efficiency and stability of a compound, the temperature is preferably 50° C. to 300° C., and particularly preferably 50° C. to 200° C.

Heating time depends on the reactivity and amount of the precursor, and is generally 0.5 min to 120 min, preferably 1 min to 60 min, and particularly preferably 1 min to 30 min.

As ambient atmosphere for performing elimination reaction can be atmosphere. The elimination reaction is preferably performed under inert gas atmosphere or reduced pressure in order to reduce any influence of side reaction such as oxidation or influence of water, and to promote removal of an eliminated component to outside the system.

Electronic Device

The specific compound of the present invention can be used in an electronic device. Examples of the electronic devices include devices having two or more electrodes in which current and voltage between the electrodes are controlled by electricity, light, magnetism, chemical materials or the like; and apparatuses for generating light, electrical field, or magnetic field by application of voltage or current. Moreover, examples thereof include elements for controlling current or voltage by application of voltage or current, elements for controlling voltage or current by application of magnetic field, and elements for controlling voltage or current by action of a chemical material. For control, rectification, switching, amplification, oscillation or the like are used.

As a device currently realized using an inorganic semiconductor such as silicon or the like, resistors, rectifiers (diode), switching elements (transistor, thyristor), amplifying elements (transistor), memory elements, chemical sensors or the like, combinations of these elements, integrated devices, or the like are exemplified. Additionally, solar batteries in which electromotive force generated by light, photodiodes for generating photocurrent, photoelements such as phototransistors or the like are used.

As an example of a preferred electronic device for applying the specific compound of the present invention, a field-effect transistor (FET) is exemplified. Hereinafter, the field-effect transistor (FET) will be specifically explained.

Transistor Configuration

FIGS. 5A to 5D show schematic configurations of organic thin-film transistors of the present invention. An organic semiconductor layer 1 of the organic thin-film transistor mainly contains the specific compound of the present invention. The organic thin-film transistor of the present invention includes a source electrode 2, a drain electrode 3 and a gate electrode 4, which are provided on the organic semiconductor layer 1 with being separated each other. A gate insulating film 5 may be provided between the gate electrode 4 and the organic semiconductor layer 1. The organic thin-film transistor is configured to control the current flowing through the organic semiconductor layer 1 between the source electrode 2 and the drain electrode 3 by applying voltage to the gate electrode 4.

The organic thin-film transistor may be formed on a substrate. As the substrate, a typical substrate formed of, for example, glass, silicon, plastic or the like may be used. A conductive substrate can be used to serve as the gate electrode. The gate electrode and the conductive substrate may be layered. However, a plastic sheet is preferably used as the substrate in case where a device, to which the organic thin-film transistor is applied, is expected to have properties such as flexibility, lightweight, lower production cost and shock resistance.

Examples of the plastic sheets include films of polyethylene terephthalate, polyethylene naphthalate, polyether sulfone, polyetherimide, polyether ether ketone, polyphenylene sulfide, polyarylate, polyimide, polycarbonate, cellulose triacetate, and cellulose acetate propionate.

Film Deposition Method: Organic Semiconductor Layer

Organic semiconductor materials used in the present invention can be film deposited by vapor phase such as vacuum deposition. Additionally, the organic semiconductor material is dissolved in a solvent such as dichloromethane, tetrahydrofuran, chloroform, toluene, chlorobenzene, dichlorobenzene and/or xylene, and applied on a substrate so as to deposit a thin film. Additionally, the thin film may be formed by application of energy to a film of the precursor so as to be transformed to a film of the specific compound. Examples of methods for depositing the organic semiconductor thin film include spray coating, spin coating, blade coating, dipping, casting, roll coating, bar coating, dye coating, inkjetting and dispensing. From the above-described deposition methods and solvents, a deposition method and solvent may be appropriately selected according to materials.

In the organic thin-film transistor of the present invention, the thickness of the organic semiconductor layer is not particularly limited, and the thickness of the organic semiconductor layer is so selected as to deposit a uniform thin film, namely, a thin film having no gaps and holes that adversely affect the carrier transportation characteristics of the organic semiconductor layer.

The thickness of the organic semiconductor layer is generally 1 µm or less, and particularly preferably 5 nm to 200 nm.

In the organic thin-film transistor of the present invention, the organic semiconductor layer deposited from the above mentioned compounds is formed contacting the source electrode, the drain electrode, and the insulating film.

Electrode

The materials of the gate electrode and the source electrode used in the organic thin-film transistor of the present invention are not particularly limited, as long as conductive materials are used. Examples thereof include platinum, gold, silver, nickel, chromium, copper, iron, tin, antimony, lead, tantalum, indium, aluminum, zinc, magnesium, and alloys thereof; conductive metal oxides such as indium/tin oxides; organic and inorganic semiconductors in which conductivity is improved by doping, etc., such as a silicon single crystal, polysilicon, amorphous silicon, germanium, graphite, polyacetylene, polyparaphenylene, polythiophene, polypyrrol, polyaniline, polythienylene vinylene, polyparaphenylene vinylene, complexes consisting of polyethylene dioxythiophene and polystyrene sulfonic acid.

Of the conductive materials described above, materials having a low electric resistance at the surface contacting the semiconductor layer are preferred for the source electrode and drain electrode.

Examples of methods for forming an electrode include a method in which a conductive thin film, which has been deposited using the material mentioned above by deposition or sputtering, is formed into an electrode by a known method such as a photolithographic method or liftoff technology; and a method in which an electrode is formed by etching a resist on a metal foil of, for example, aluminum and copper, by thermal transfer, inkjet or the like. In addition, an electrode may be formed by directly patterning by inkjet printing using a solution or dispersion liquid of a conductive polymer or a dispersion liquid of conductive particles, or may be formed from a coated layer by lithography or laser ablation. It is also possible to use a method in which an ink, conductive paste, etc. containing conductive polymers or conductive particles are patterned by a printing method such as relief printing, intaglio printing, planographic printing or screen printing.

The organic thin-film transistor of the present invention can have an extraction electrode from each electrode if necessary.

Insulating Film

The insulating film used in the organic thin-film transistor of the present invention is formed from various materials for insulating film. Examples thereof include inorganic insulating materials such as silicon oxide, silicon nitride, aluminum oxide, aluminum nitride, titanium oxide, tantalum oxide, tin oxide, vanadium oxide, barium-strontium-titanium oxide, barium-titanium-zirconium oxide, lead-zirconium-titanium oxide, lead lanthanum titanate, strontium titanate, barium titanate, barium magnesium fluoride, bismuth-niobium-tantalum oxide and yttrium trioxide.

Additionally, examples thereof include polymer compounds such as polyimides, polyvinyl alcohols, polyvinyl phenols, polyesters, polyethylene, polyphenylenesulfides, unsubstituted or halogen atom substituted polyparaxylylene, polyacrylonitrile and cyanoethylpullulan.

These insulating materials may be used in combination. The insulating material is not particularly limited, and it is preferred to select an insulating material having a high dielectric constant and a low conductivity.

Examples of the methods of depositing the insulating film using the insulating materials include dry deposition processes such as a chemical vacuum deposition (CVD), a plasma CVD and a plasma polymerization; and wet coating processes such as spray coating, spin coating, dip coating, inkjetting, casting, blade coating and bar coating.

Modification of Interface Between Organic Semiconductor and Insulating Film

In the organic thin-film transistor of the present invention, the organic thin film may be provided between the insulating film and the organic semiconductor layer to improve adhesiveness thereof, decrease gate voltage and reduce leak current. The organic thin film is not particularly limited as long as the organic thin film does not have a chemical effect on an organic semiconductor layer. For example, an organic molecular film and a polymer thin film can be used.

As the organic molecular film, coupling agents such as octyltrichlorosilane, octadecyl trichlorosilane, hexamethylene disilazane and phenyltrichlorosilane may be used. In addition, as the polymer thin film, the aforementioned polymer insulating materials can be used, and these may function as a sort of the insulating film. This organic thin film may be subject to an anisotropic treatment by rubbing or the like.

Protective Layer

The organic thin-film transistor of the present invention can be stably driven in the atmosphere. If necessary, a protective layer can be provided in terms of protection from mechanical destruction and moisture and/or gas, and protection for integration of a device for convenience.

Applied Device

The organic thin-film transistors of the present invention can be utilized as an element for driving image display elements such as liquid crystal, organic electroluminescence, and electrophoretic migration. When such elements are integrated, it is possible to produce a display referred to as "electronic paper". Moreover, it is also possible to use an IC in which the organic thin-film transistors of the present invention are integrated as a device such as an IC tag.

EXAMPLES

Hereinafter, the present invention will be specifically explained with reference to Examples. However, the present invention will not be limited by these Examples as long as not exceeding the gist of the present invention.

Hereinafter, a [1]benzothieno[3,2-b]benzothiophene compound of the present invention is also called as "specific compound" in Examples. Moreover, a precursor of the specific compound is called as "precursor".

Synthesis Example 1

Synthesis of Intermediate of Specific Compound (1) Synthesis of a [1]benzothieno[3,2-b][1]benzothiophene Unit A dihalogen derivative of [1]benzothieno[3,2-b][1]benzothiophene used for production of a compound of the present invention was obtained according to a process of Scheme 1 with reference to Zh. Org. Khim., 16, 2, 383 (1980) and J. Am. Chem. Soc. 128, 12604 (2006). Thus, Dihalogen Derivative 7 was obtained in an amount of 5 g and yield of 30.5%.

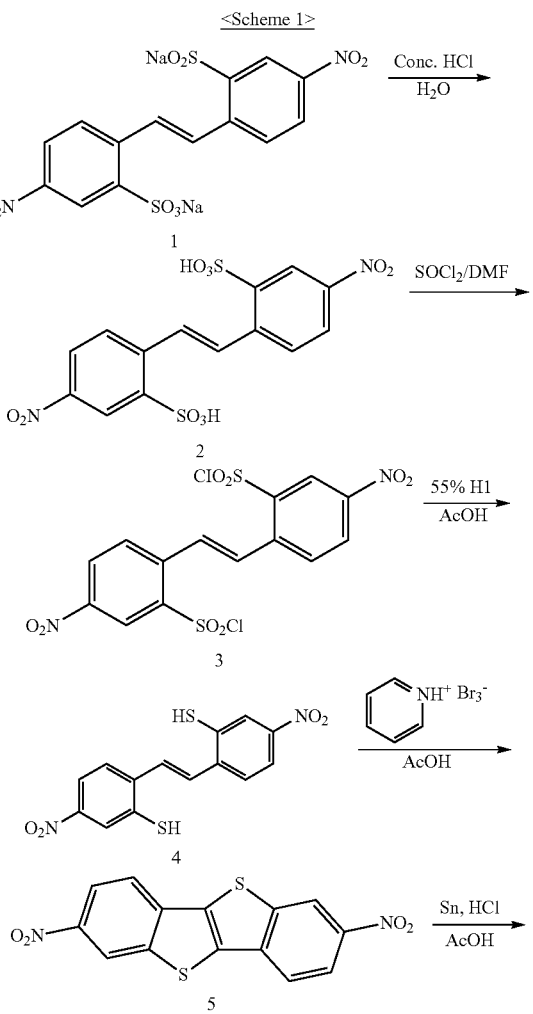

29
-continued

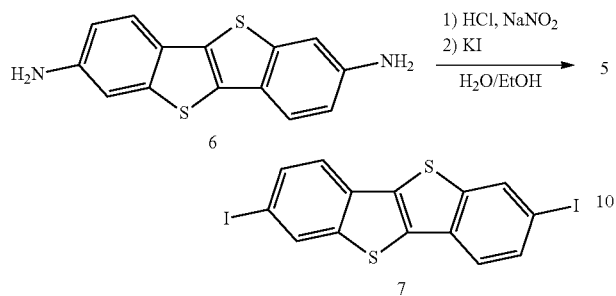

The analysis result of Dihalogen Derivative 7 of Scheme 1 was as follows.

$^1$H NMR (400 MHz, CDCl$_3$, TMS, δ): 7.62 (d, 2H, J=8.4 Hz), 7.75 (dd, 2H, J$_1$=8.4 Hz, J$_2$=1.4 Hz), 8.26 (d, 2H, J=1.4 Hz).

Mass spectrometry: GC-MS m/z=492 (M+)
Elemental analysis value

|   | Found value (%) | Calculated value (%) |
|---|---|---|
| C | 34.40 | 34.17 |
| H | 1.19 | 1.23 |

Melting point: 300° C. or more

From the above analysis result, it was confirmed that a structure of the synthesized product did not contradict that of Derivative 7.

(2) Synthesis of Soluble Leaving Group Unit

A soluble leaving group unit for production of the specific compound of the present invention was synthesized with reference to Chem. Mater. 16, 4783 (2004) and J. Am. Chem. Soc. 126, 1596 (2006), according to Schemes 2 to 5.

<Scheme 2>
Synthesis of Tributyltin Derivative 11 (8→11)

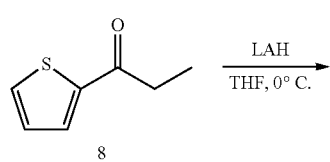

30
-continued

By the process of Scheme 2, as a colorless liquid Tributyltin Derivative 11 was obtained in an amount of 5.8 g and yield of 77%.

The analysis result of Tributyltin Derivative 11 was as follows.

$^1$H NMR (500 MHz, CDCl$_3$, TMS, δ): 7.13 (d, 1H, J=2.9 Hz), 7.00 (d, 1H, J=3.5 Hz), 6.03 (t, 1H, J=4 Hz), 2.29-2.36 (m, 1H), 1.89-2.05 (m, 2H), 1.50-1.64 (m, 6H), 1.37-1.45 (m, 2H), 1.31-1.36 (m, 6H), 1.11-1.28 (m, 12H), 1.08 (t, J=8.0 Hz, 6H), 0.95 (t, J=7.5 Hz, 3H), 0.78-0.90 (m, 15H).

Mass spectrometry: GC-MS m/z=614 (M+)

From the above analysis result, it was confirmed that a structure of the synthesized product did not contradict that of Derivative 11.

<Scheme 3>
Synthesis of Boroniate Ester Derivative 15 (12→15)

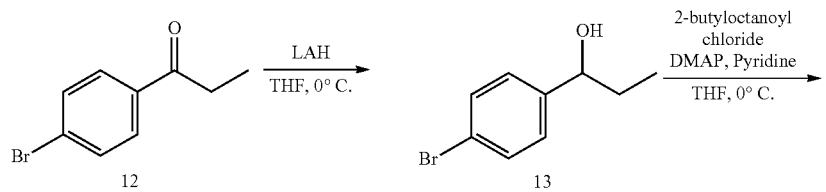

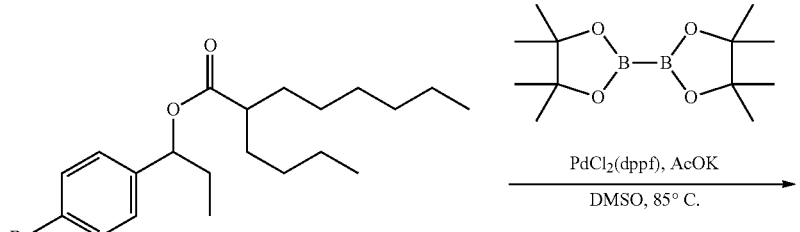

As a pale yellow viscous liquid Boronate Ester Derivative 15 was obtained in an amount of 7.38 g and yield of 94.0%.

The analysis result of Boronate Ester Derivative 15 was as follows.

$^1$H NMR (500 MHz, CDCl$_3$, TMS, δ): 7.77 (d, J=8.0 Hz, 2H), 7.31 (d, J=8.0 Hz, 2H), 5.68 (t, J=6.9 Hz, 1H), 2.32-2.38 (m, 1H), 1.85-1.93 (m, 1H), 1.78-1.84 (m, 1H), 1.53-1.62 (m, 2H), 1.37-1.47 (m, 2H), 1.33 (s, 12H), 1.1-1.32 (m, 12H), 0.79-0.91 (m, 9H).

Mass spectrometry: GC-MS m/z=444 (M+)

From the above analysis result, it was confirmed that a structure of the synthesized product did not contradict that of Derivative 15.

<Scheme 3>
Synthesis of Tributyltin Derivative 20 (16 → 20)

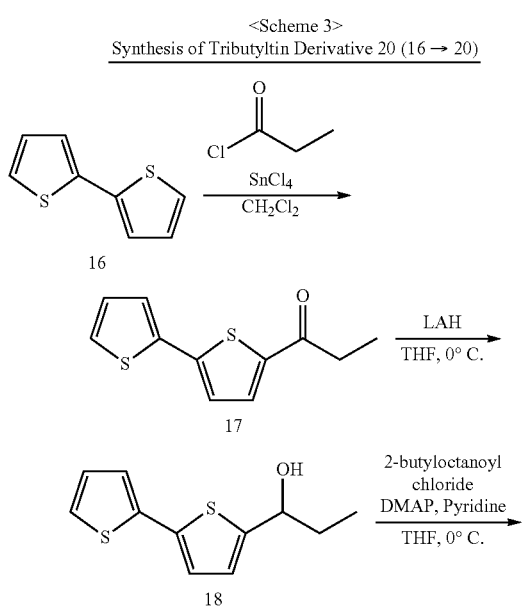

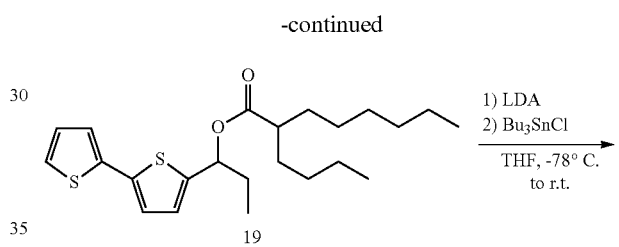

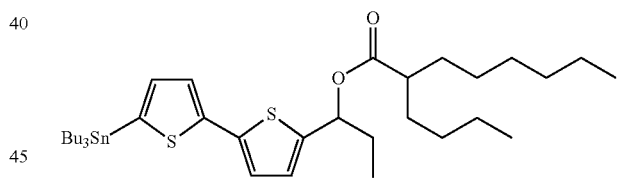

As a yellow viscous liquid Tributyltin Derivative 20 was obtained in an amount of 8.6 g and yield of 95%.

The analysis result of Derivative 20 was as follows.

$^1$H NMR (500 MHz, CDCl$_3$, TMS, δ): 7.25 (d, J=3.4 Hz, 1H), 7.04 (d, J=4.0 Hz, 1H), 7.00 (d, J=3.4 Hz, 1H), 6.92 (d, J=4.0 Hz, 1H), 5.92 (t, J=6.9 Hz, 1H), 2.31-2.37 (m, 1H), 1.88-2.05 (m, 2H), 1.54-1.64 (m, 6H), 1.38-1.47 (m, 2H), 1.31-1.38 (m, 6H), 1.14-1.28 (m, 12H), 1.11 (t, J=8.0 Hz, 6H), 0.97 (t, J=7.5 Hz, 3H), 0.90 (t, J=7.5 Hz, 6H), 0.78-0.86 (m, 9H).

Mass spectrometry: GC-MS m/z=696 (M+)

From the above analysis result, it was confirmed that a structure of the synthesized product did not contradict that of Derivative 20.

Scheme 5
Synthesis of Tributyltin Derivative 22 (9 → 22)

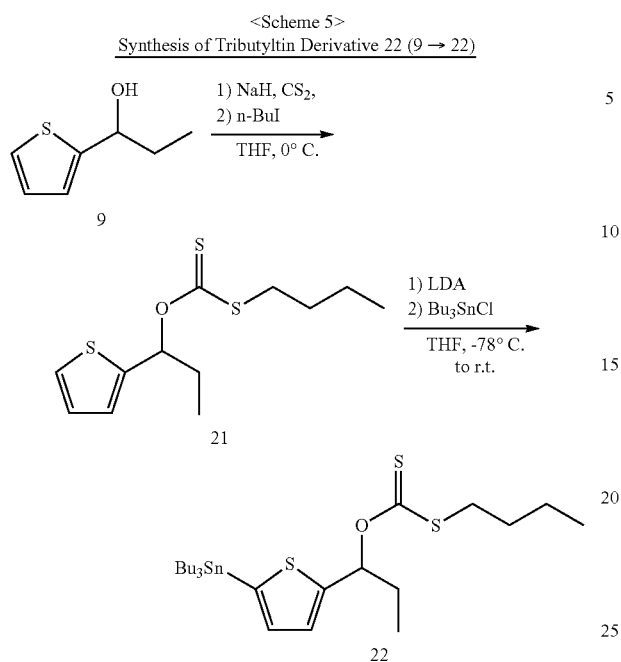

As a yellow liquid Tributyltin Derivative 22 was obtained by the process of Scheme 5 in an amount of 3.33 g and yield of 81%.

The analysis result of Derivative 22 was as follows.

$^1$H NMR (500 MHz, CDCl$_3$, TMS, δ): 7.08 (d, 1H, J=3.2 Hz), 6.97 (d, 1H, J=3.2 Hz), 5.01 (t, 1H, J=4 Hz), 2.99 (td, J$_1$=7.2 Hz, J$_2$=2.0 Hz, 2H), 2.03-2.10 (quint, J=7.2 Hz, 2H), 1.52-1.64 (m, 6H), 1.28-1.43 (m, 10H), 1.08 (t, J=8.0 Hz, 6H), 0.99 (t, J=7.5 Hz, 3H), 0.87-0.94 (m, 12H).

Mass spectrometry: GC-MS m/z=564 (M+)

From the above analysis result, it was confirmed that a structure of the synthesized product did not contradict that of Derivative 22.

(3) Synthesis of Unit Having Alkenyl Group

A boronate ester unit having an alkenyl group was synthesized according to Scheme 6.

Scheme 6
Synthesis of Alkenyl Boronate Ester Derivative 26 (23→26)

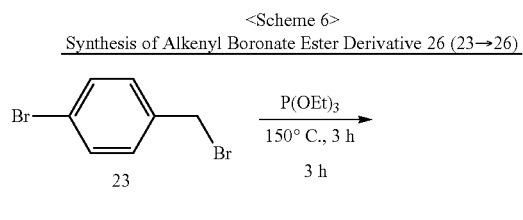

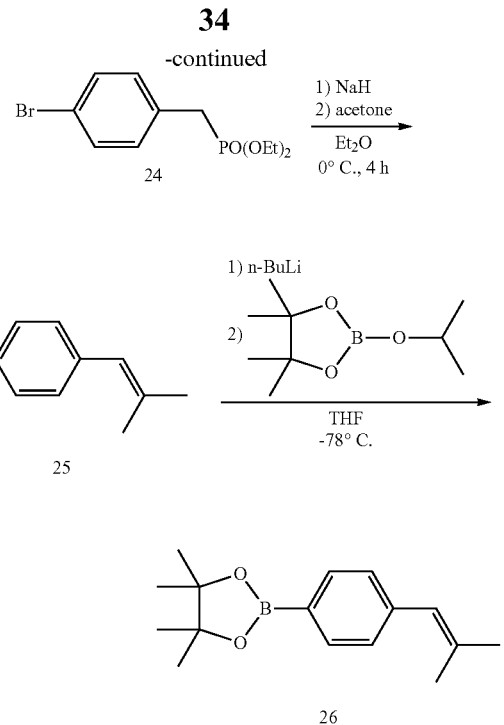

As a pale yellow liquid Boronate Ester Derivative 26 was obtained in an amount of 2.61 g and yield of 68.0%.

The analysis result of Boronate Ester Derivative 26 was as follows.

$^1$H NMR (500 MHz, CDCl$_3$, TMS, δ): 7.75 (d, J=8.1 Hz, 2H), 7.23 (d, J=8.0 Hz, 2H), 6.28 (s, 1H), 1.93 (dd, J$_1$=19.4, 1.5 Hz, J$_2$=1.5 Hz, 6H), 1.34 (s, 12H).

Mass spectrometry: GC-MS m/z=258 (M+)

From the above analysis result, it was confirmed that a structure of the synthesized product did not contradict that of Derivative 26.

In Schemes 1 to 6, DMF represents dimethylformamide, THF represents tetrahydronaphthalene, LAH represents lithium aluminum hydride, LDA represents lithium diisopropylamide, DMAP represents N,N-dimethylaminopyridine, DMSO represents dimethyl sulfoxide, AcOK represents potassium acetate, and PdCl$_2$(dppf) represents dichloro[1,1-bis(diphenylphosphino)ferrocene]palladium.

By use of each of the units synthesized in the synthesis Examples, the following Examples were performed.

Example 1

Synthesis of Precursor 1

Precursor 1 was synthesized according to Scheme 7.

Scheme 7

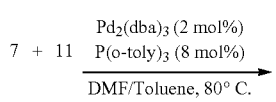

-continued

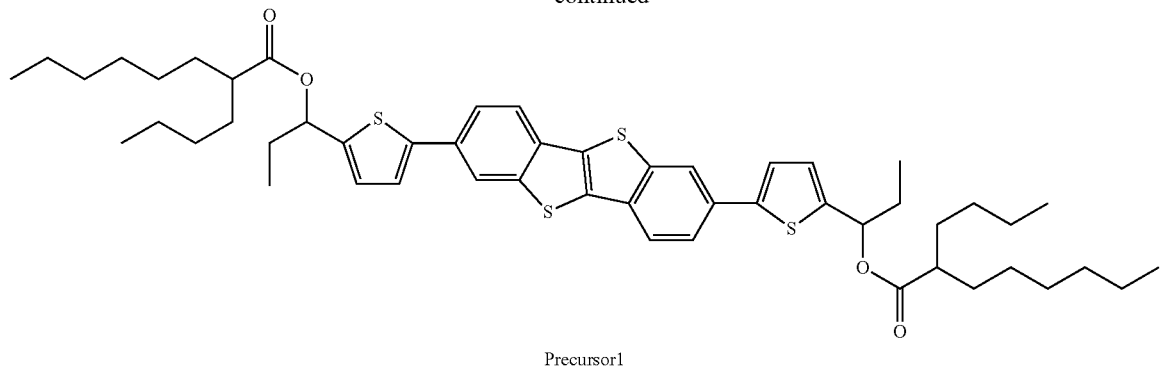

Precursor1

A three-necked flask was charged with Derivative 7 (492.5 mg, 1 mmol), Derivative 11 (1,299 mg, 2.1 mmol), and dimethylformamide (hereinafter referred to as DMF)/toluene (10 mL, 1/1=v/v), bubbled with argon gas for 30 minutes, and then further charged with $Pd_2(dba)_3$ (2 mol %, 18.3 mg), P(o-toly)$_3$ (8 mol %, 24.4 mg), DMF/toluene (4 mL), bubbled with argon gas for 10 minutes, and heated at 80° C. (±5° C.) for 12 hours. The three-necked flask was cooled to a room temperature, and charged with toluene (100 mL) and a saturated saline solution (200 mL) to separate an organic phase. From a residual liquid an aqueous phase was extracted with toluene (50 mL) for three times. The residual organic phase was added to the separated organic phase, and washed with a saturated aqueous potassium fluoride solution (200 mL), and further washed with a saturated saline solution for three times. The organic phase was dried with magnesium sulfate, and a filtrate was concentrated to obtain a brown solid.

The brown solid was subjected to column purification using toluene as an eluant to obtain an orange solid in an amount of 800 mg. The orange solid was further subjected to recycle GPC using tetrahydrofuran (hereinafter referred to as THF), manufactured by NIPPON BUNSEKI Co., Ltd., as an eluant to obtain a yellow crystal (amount: 500 mg, yield: 56.5%).

The analysis result of the obtained Precursor 1 was as follows.

$^1$H NMR (500 MHz, $CDCl_3$, TMS, δ): 8.09 (d, 2H, J=0.85 Hz), 7.84 (d, 1H, J=4.2 Hz), 7.4 (dd, 2H, J=0.85 Hz, $J_2$=4.2 Hz), 7.25 (d, 2H, J=1.9 Hz), 7.04 (d, 2H, J=1.9 Hz), 5.97 (t, 2H, J=6.9 Hz), 2.34-2.37 (m, 2H), 1.96-2.07 (m, 4H), 1.60-1.67 (m, 4H), 1.40-1.46 (m, 4H), 1.13-34 (m, 24H), 1.01 (t, 6H, J=7.2 Hz), 0.78-0.85 (m, 12H).

Mass spectrometry: GC-MS m/z=884 (M+)

Elemental analysis value

| | Found value (%) | Calculated value (%) |
|---|---|---|
| C | 70.40 | 70.54 |
| H | 7.94 | 7.74 |
| S | 14.2 | 14.49 |

Melting point: 93.2° C. to 94.2° C.

From the above result, it was confirmed that a structure of the synthesized product did not contradict that of Precursor 1.

Example 2

Synthesis of Precursor 2

Precursor 2 was synthesized according to Scheme 8.

<Scheme 8>

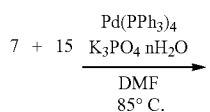

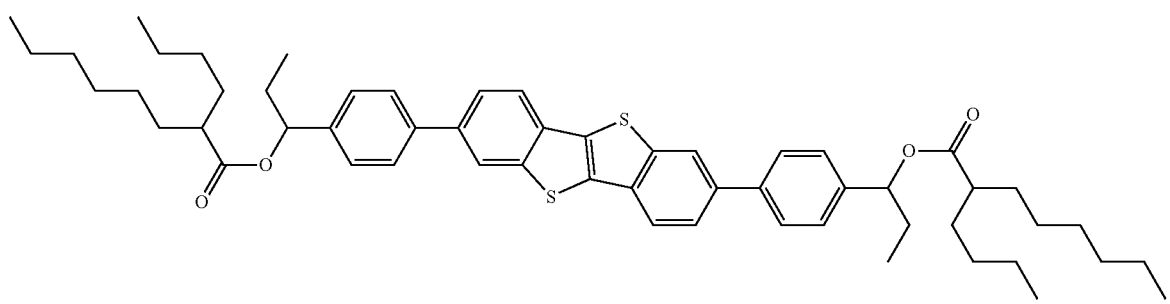

Precursor2

A three-necked flask was charged with Derivative 7 (1,968 mg, 4.0 mmol), Derivative 15 (4,089 mg, 9.2 mmol), K₃PO₄.nH₂O (13.6 g) and DMF (80 mL), bubbled with argon gas for 30 minutes, and then further charged with Pd(PPh₃)₄ (368 mg, 0.4 mmol), bubbled with argon gas for 10 minutes, and heated at 85° C. (±5° C.) for 9 hours. The three-necked flask was cooled to a room temperature, and the content was subjected to celite filtration, and then celite was washed with From the above result, it was confirmed that a structure of the synthesized product did not contradict that of Precursor 2.

Example 3

Synthesis of Precursor 3

Precursor 3 was synthesized according to Scheme 9.

<Scheme 9>

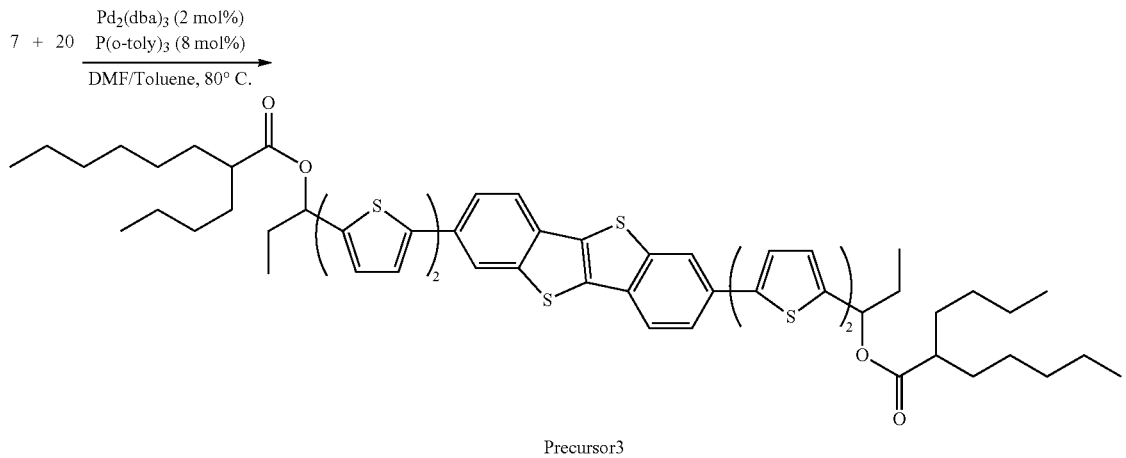

Precursor3 toluene (100 mL). The filtrate was poured into a saturated aqueous ammonium chloride solution (400 mL), and toluene (200 mL) was added therein to separate an organic phase. From a residual liquid an aqueous phase was extracted with toluene (50 mL) for three times. The residual organic phase was added to the separated organic phase, and washed with a saturated saline solution for three times. The organic phase was dried with magnesium sulfate, and a filtrate was concentrated to obtain a red solid in an amount of 1,020 mg.

The red solid was subjected to column purification using toluene/hexane (6/4→10/0) as an eluant to obtain a yellow solid (amount: 2.38 g, yield: 66.0%). A part of the yellow solid (800 mg) was further subjected to recycle GPC using THF manufactured by NIPPON BUNSEKI Co., Ltd. as an eluant to obtain a pale yellow crystal (amount: 708 mg, yield: 88.5%).

The analysis result of the obtained Precursor 2 was as follows.

$^1$H NMR (500 MHz, CDCl₃, TMS, δ): 8.12 (d, J=1.2 Hz, 2H), 7.94 (d, J=8.0 Hz, 2H), 7.69 (dd, J=8.6 and 1.7 Hz), 7.66 (d, J=8.0 Hz, 4H), 7.44 (d, J=8.0 Hz, 4H), 5.74 (t, J=7.4 Hz, 2H), 2.36-2.42 (m, 2H), 1.95-2.25 (m, 2H), 1.83-1.91 (m, 2H), 1.57-1.68 (m, 4H), 1.40-1.50 (m, 4H), 1.14-1.36 (m, 24H), 0.96 (t, J=7.50 Hz, 6H), 0.82-0.88 (m, 12H).

Mass spectrometry: GC-MS m/z=872 (M+)

Elemental analysis value

|   | Found value (%) | Calculated value (%) |
|---|---|---|
| C | 76.90 | 77.02 |
| H | 8.54 | 8.31 |
| S | 7.20 | 7.34 |

Melting point: 87.5° C. to 90.0° C.

A three-necked flask was charged with Derivative 7 (492.5 mg, 1 mmol), Derivative 20 (1,460 mg, 2.1 mmol), and DMF/toluene (10 mL, 1/1=v/v), bubbled with argon gas for 30 minutes, and then further charged with Pd₂(dba)₃ (2 mol %, 18.3 mg), P(o-toly)₃ (8 mol %, 24.4 mg), DMF/toluene (6 mL, 1/1=v/v), bubbled with argon gas for 10 minutes, and heated at 80° C. (±5° C.) for 9 hours. The three-necked flask was cooled to a room temperature, and precipitation was filtrated and washed with methanol and hexane. The precipitation was dissolved in chloroform, and a filtrate passed through a silica gel pad was dried to obtain an orange crystal (amount: 840 mg, yield: 80.0%).

The analysis result of the obtained Precursor 3 was as follows.

$^1$H NMR (500 MHz, CDCl₃, TMS, δ): 8.17 (d, J=1.7 Hz, 2H), 7.87 (d, J=8.0 Hz, 2H), 7.70 (dd, J₁=1.7 Hz, J₂=8.0 Hz, 2H), 7.32 (d, J=4.0 Hz, 2H), 7.15 (d, J=3.4 Hz, 2H), 7.07 (d, J=3.4 Hz, 21H), 6.97 (d, J=3.4 Hz, 2H), 5.94 (t, J=6.9 Hz, 2H), 2.32-2.39 (m, 2H), 1.91-2.08 (m, 4H), 1.57-1.66 (m, 4H), 1.40-1.49 (m, 4H), 1.11-1.36 (m, 24H), 0.99 (t, J=6.9 Hz, 6H), 0.81-0.90 (m, 12H).

Mass spectrometry: GC-MS m/z=1,050 (M+)

Elemental analysis value

|   | Found value (%) | Calculated value (%) |
|---|---|---|
| C | 68.26 | 68.19 |
| H | 6.91 | 6.71 |
| S | 18.93 | 18.83 |

Melting point: 134.0° C. to 135.4° C.

From the above result, it was confirmed that a structure of the synthesized product did not contradict that of Precursor 3.

Example 4

Synthesis of Precursor 4

Precursor 4 was synthesized according to Scheme 10.

<Scheme 10>

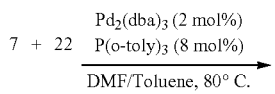

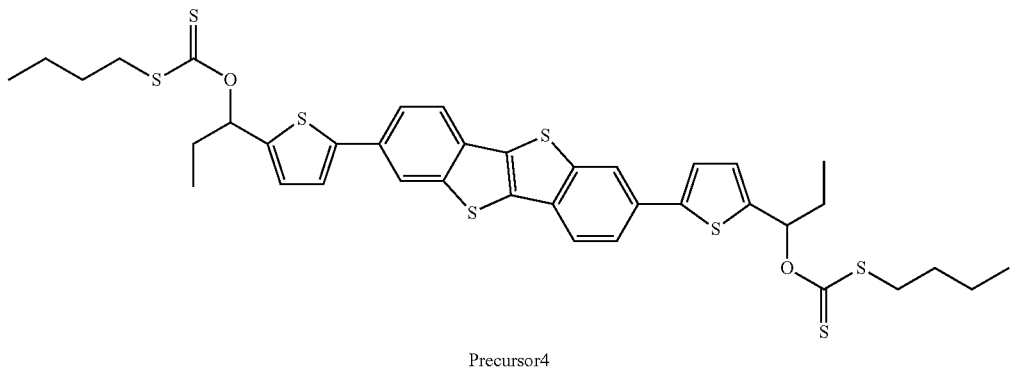

Precursor4

A three-necked flask was charged with Derivative 7 (492.5 mg, 1 mmol), Derivative 22 (1,183 mg, 2.1 mmol) and DMF/toluene (10 mL, 1/1=v/v), bubbled with argon gas for 30 minutes, and then further charged with Pd$_2$(dba)$_3$ (2 mol %, 18.3 mg), P(o-toly)$_3$ (8 mol %, 24.4 mg) and DMF/toluene (4 mL), bubbled with argon gas for 10 minutes, and heated at 80° C. (±5° C.) for 12 hours. The three-necked flask was cooled to a room temperature, and charged with toluene (100 mL) and a saturated saline solution (200 mL) to separate an organic phase. From a residual liquid an aqueous phase was extracted with toluene (50 mL) for three times. The residual organic phase was added to the separated organic phase, and washed with a saturated aqueous potassium fluoride solution (200 mL), and further washed with a saturated saline solution for three times. The organic phase was dried with magnesium sulfate, and a filtrate was concentrated to obtain a brown solid.

The brown solid was subjected to column purification using toluene as an eluant to obtain an orange solid in an amount of 590 mg. The orange solid was further subjected to recycle GPC using THF, manufactured by NIPPON BUN-SEKI Co., Ltd., as an eluant to obtain a yellow crystal (amount: 435 mg, yield: 57.8%).

The analysis result of the obtained Precursor 4 was as follows.

Mass spectrometry: GC-MS m/z=614 (M+)

Elemental analysis value

|   | Found value (%) | Calculated value (%) |
|---|---|---|
| C | 60.15 | 60.60 |
| H | 5.68 | 5.35 |
| S | 29.30 | 29.80 |

From the above result, it was confirmed that a structure of the synthesized product did not contradict that of Precursor 4.

Example 5

Synthesis of Specific Compound 1

Specific Compound OSC 1 was synthesized from Precursor 1 according to Scheme 11.

<Scheme 11>

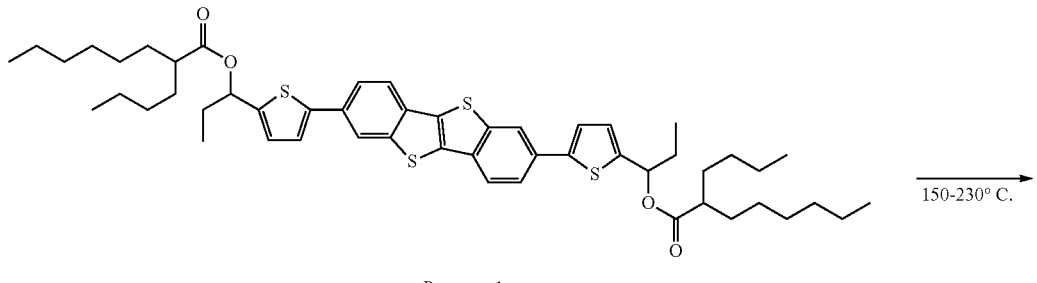

Precursor1

150-230° C.

-continued

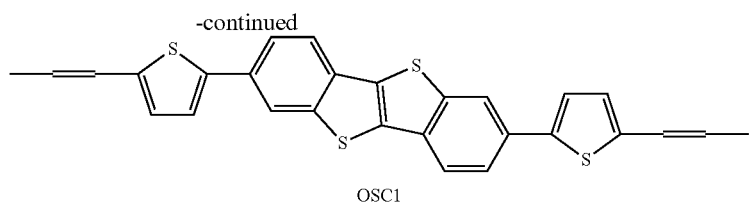

OSC1

Precursor 1 (1.5 g, 1.7 mmol) was put in a quartz boat (width: 20 mm, length: 92 mm, height: 11 mm) and heated on a hot plate at 230° C. for 3 hours to obtain a solid. The solid was ground in a mortar, washed with toluene, ethyl acetate, hexane and methanol, and vacuum-dried to obtain a brownish yellow solid in an amount of 700 mg. Finally, the obtained solid was purified by a temperature gradient sublimation method (source temperature: 330° C., pressure: up to $10^{-4}$ Pa) so as to obtain Specific Compound OSC 1 as a yellow crystal (amount: 100 mg, yield: 12.1%).

The analysis result of the obtained Specific Compound OSC 1 was as follows.

Mass spectrometry: GC-MS m/z=484 (M+)

Elemental analysis value

|   | Found value (%) | Calculated value (%) |
|---|---|---|
| C | 69.38 | 69.22 |
| H | 4.16 | 4.26 |
| S | 26.46 | 26.52 |

Decomposition point: 406° C.

From the above result, it was confirmed that a structure of the synthesized product did not contradict that of Specific Compound OSC 1.

Example 6

Synthesis of Specific Compound 2

Specific Compound OSC 2 was synthesized from Precursor 2 according to Scheme 12.

Precursor 2 (1.5 g, 1.7 mmol) was put in a quartz boat (width: 20 mm, length: 92 mm, height: 11 mm) and heated on a hot plate at 220° C. for 3 hours to obtain a solid. The solid was ground in a mortar, washed with toluene, ethyl acetate, hexane and methanol, and vacuum-dried to obtain a brownish yellow solid in an amount of 655 mg. Finally, the obtained solid was purified by a temperature gradient sublimation method (source temperature: 340° C., pressure: up to $10^{-4}$ Pa) so as to obtain Specific Compound OSC 2 as a yellow crystal (amount: 160 mg, yield: 19.3%).

The analysis result of the obtained Specific Compound OSC 2 was as follows.

Mass spectrometry: GC-MS m/z=472 (M+)

Elemental analysis value

|   | Found value (%) | Calculated value (%) |
|---|---|---|
| C | 81.11 | 81.31 |
| H | 5.26 | 5.12 |
| S | 13.51 | 13.57 |

Decomposition point: 382° C.

From the above result, it was confirmed that a structure of the synthesized product did not contradict that of Specific Compound OSC 2.

Example 7

Synthesis of Specific Compound 3

Specific Compound OSC 3 was synthesized from Precursor 3 according to Scheme 13.

<Scheme 12>

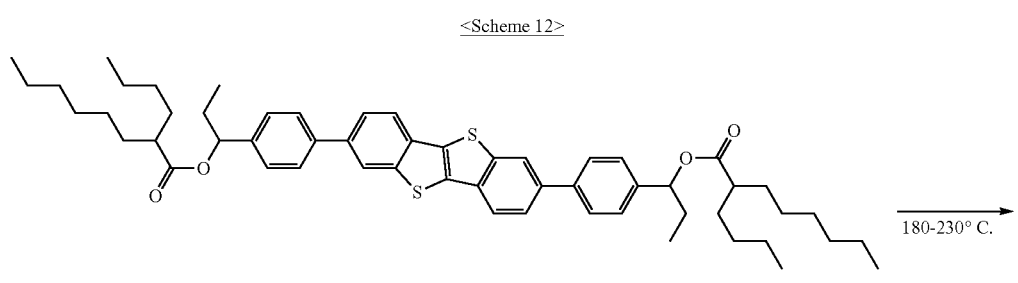

Precursor2

180-230° C.

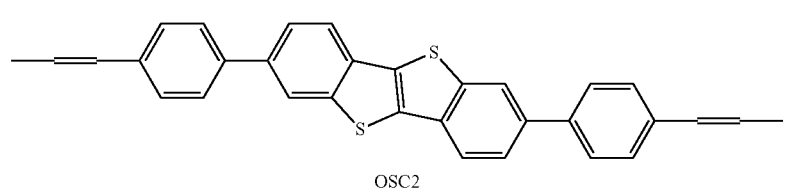

OSC2

<Scheme 13>

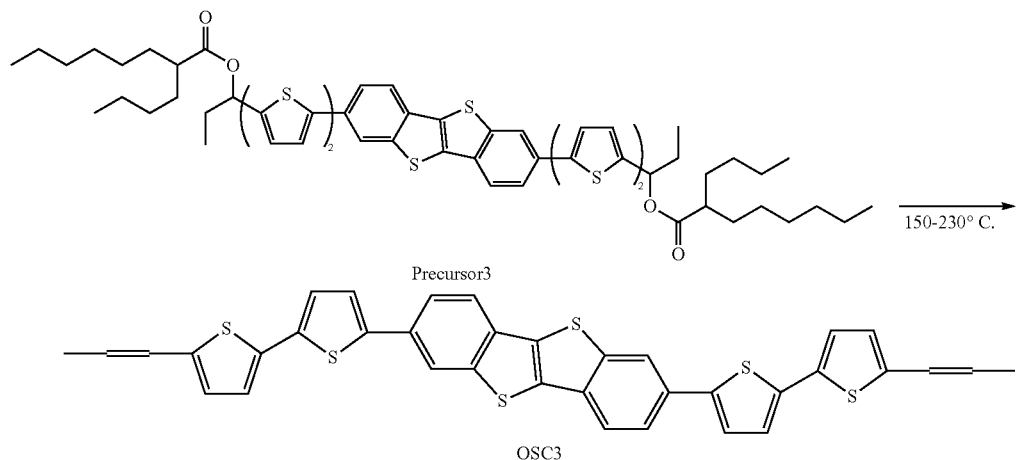

Precursor3

OSC3

Precursor 3 (500 mg, 0.48 mmol) was put in a quartz boat (width: 20 mm, length: 92 mm, height: 11 mm) and heated on a hot plate at 220° C. for 3 hours to obtain a solid. The solid was ground in a mortar, washed with toluene, ethyl acetate, hexane and methanol, and vacuum-dried to obtain a brownish yellow solid in an amount of 290 mg. Finally, the obtained solid was purified by a temperature gradient sublimation method (source temperature: 370° C., pressure: up to $10^{-4}$ Pa) so as to obtain Specific Compound OSC 3 as a yellow crystal (amount: 70 mg, yield: 22.7%).

The analysis result of the obtained Specific Compound OSC 3 was as follows.

Mass spectrometry: GC-MS m/z=648 (M+)

Elemental analysis value

|   | Found value (%) | Calculated value (%) |
|---|---|---|
| C | 66.43 | 66.63 |
| H | 3.92 | 3.73 |
| S | 29.45 | 29.65 |

Decomposition point: 402° C.

From the above result, it was confirmed that a structure of the synthesized product did not contradict that of Specific Compound OSC 3.

Example 8

Synthesis of Specific Compound 4

Specific Compound OSC 4 was synthesized according to Scheme 14.

<Scheme 14>

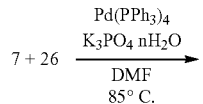

-continued

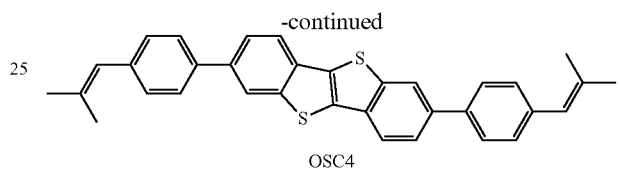

OSC4

A three-necked flask was charged with Derivative 7 (984 mg, 2.0 mmol), Derivative 26 (1,135 mg, 4.4 mmol), $K_3PO_4 \cdot nH_2O$ (6.8 g) and DMF (40 mL), bubbled with argon gas for 30 minutes, and then further charged with $Pd(PPh_3)_4$ (184 mg, 0.2 mmol), bubbled with argon gas for 10 minutes, and heated at 85° C. (±5° C.) for 10 hours. The three-necked flask was cooled to a room temperature, and the content was poured into a saturated aqueous ammonium chloride solution (200 mL), and precipitation was filtrated, washed with methanol, and vacuum-dried to obtain a yellow solid in an amount of 900 mg.

Finally, the obtained solid was purified by a temperature gradient sublimation method (source temperature: 340° C., pressure: up to $10^{-4}$ Pa) so as to obtain Specific Compound OSC 4 as a yellow crystal (amount: 120 mg, yield: 12.0%).

The analysis result of the obtained Specific Compound OSC 4 was as follows.

Mass spectrometry: GC-MS m/z=500 (M+)

Elemental analysis value

|   | Found value (%) | Calculated value (%) |
|---|---|---|
| C | 81.41 | 81.56 |
| H | 5.76 | 5.64 |
| S | 12.51 | 12.81 |

Decomposition point: 414° C.

From the above result, it was confirmed that a structure of the synthesized product did not contradict that of Specific Compound OSC 4.

Example 9

Synthesis of Specific Compound 5

Specific Compound OSC 5 was synthesized according to Scheme 15.

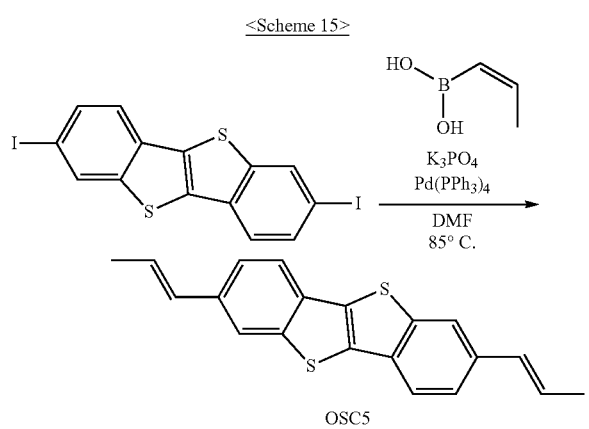

Scheme 15

OSC5

A three-necked flask was charged with Derivative 7 (984 mg, 2.0 mmol), cis-1-propenyl boronate (1,135 mg, 4.4 mmol), $K_3PO_4 \cdot nH_2O$ (6.8 g), DMF (40 mL), bubbled with argon gas for 30 minutes, and then further charged with $Pd(PPh_3)_4$ (0.2 mmol, 184 mg), bubbled with argon gas for 10 minutes, and heated at 85° C. (±5° C.) for 8 hours. The three-necked flask was cooled to a room temperature, and the content was subjected to celite filtration, and then celite was washed with toluene (100 mL). The filtrate was poured into a saturated aqueous ammonium chloride solution (200 mL), and toluene (200 mL) was added therein to separate an organic phase. From a residual liquid an aqueous phase was extracted with toluene (50 mL) for three times. The residual organic phase was added to the separated organic phase, and washed with a saturated saline solution for three times. The organic phase was dried with magnesium sulfate, and a filtrate was concentrated to obtain a brown solid.

The brown solid was subjected to column purification using dichloromethane/hexane (1/3) as an eluant to obtain a colorless solid (amount: 380 mg). The solid was recrystallized from an ethyl acetate solution to obtain a pale yellow crystal (amount: 300 mg).

Finally, the obtained solid was purified by a temperature gradient sublimation method (source temperature: 185° C., pressure: up to $10^{-4}$ Pa) so as to obtain Specific Compound OSC 5 as a yellow crystal (amount: 100 mg, yield: 15.6%).

The analysis result of the obtained Specific Compound OSC 5 was as follows.

$^1$H NMR (500 MHz, $CDCl_3$, TMS, δ): 7.81 (d, J=1.2 Hz, 2H), 7.76 (d, J=8.0 Hz, 2H), 7.46 (dd, J=8.3 Hz and 1.2 Hz, 2H), 6.52 (dd, J=16 Hz and 1.7 Hz, 2H), 6.35 (dq, J=6.3 Hz and 2.6 Hz, 2H), 1.94 (dd, J=6.3 Hz and 1.7 Hz, 6H).

Mass spectrometry: GC-MS m/z=320 (M+)

Elemental analysis value

|   | Found value (%) | Calculated value (%) |
|---|---|---|
| C | 81.41 | 81.56 |
| H | 5.76 | 5.64 |
| S | 12.51 | 12.81 |

Melting point: 246.0° C. to 246.6° C.

From the above result, it was confirmed that a structure of the synthesized product did not contradict that of Specific Compound OSC 5.

Example 10

Synthesis of Specific Compound 6

Specific Compound OSC 1 was synthesized from Precursor 4 according to Scheme 16.

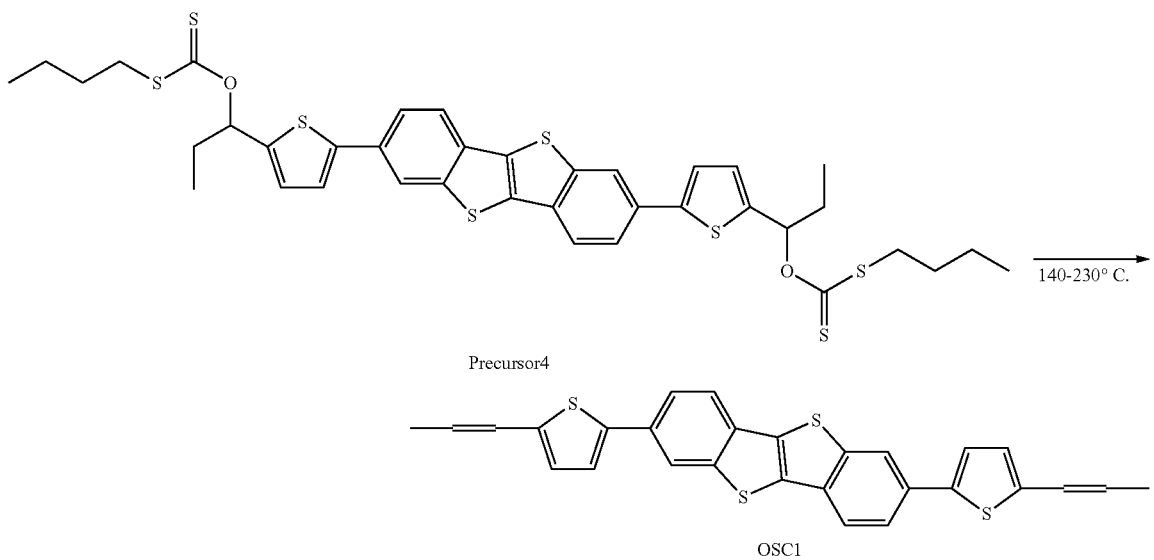

Scheme 16

Precursor4

OSC1

Precursor 4 (0.5 g, 0.664 mmol) was put in a quartz boat (width: 20 mm, length: 92 mm, height: 11 mm) and heated on a hot plate at 160° C. for 2 hours to obtain a solid. The solid was ground in a mortar, washed with toluene, ethyl acetate, hexane and methanol, and vacuum-dried to obtain a brownish yellow solid in an amount of 200 mg. Finally, the obtained solid was purified by a temperature gradient sublimation method (source temperature: 330° C., pressure: up to $10^{-4}$ Pa) so as to obtain Specific Compound OSC 1 as a yellow crystal (amount: 53 mg, yield: 16.5%), similar to Example 5.

The analysis result of the obtained Specific Compound OSC 1 was as follows.

Mass spectrometry: GC-MS m/z=484 (M+)

Elemental analysis value

|   | Found value (%) | Calculated value (%) |
|---|---|---|
| C | 69.28 | 69.22 |
| H | 4.39 | 4.26 |
| S | 26.42 | 26.52 |

Decomposition point: 407° C.

From the above result, it was confirmed, in the same manner as in Example 5, that a structure of the synthesized product did not contradict that of Specific Compound OSC 1.

As is clear from Examples 1 to 10, the precursor molecule of the present invention can be transformed to a specific compound of the present invention by heating.

Example 11

Observation of Elimination Behavior of Precursor Synthesized in Example 1

Precursor 1 synthesized in Example 1 (5 mg) was heated on a silicon wafer which was placed on a hot plate at 200° C. and 330° C. for 30 minutes so as to prepare a sample. IR spectra (KBr method, SPECTRUM GX FT-IR SYSTEM manufactured by PerkinElmer, Inc.) of the sample, a precursor before heating and 2-butyloctanoic acid produced by elimination reaction were measured. The results are shown in FIG. 1.

FIG. 1 shows the IR spectrum of a precursor of the present invention heated at a room temperature, that of a precursor of the present invention heated at 200° C., that of a precursor of the present invention heated at 330° C., and that of 2-butyloctanoic acid, in this order from the top.

It was observed that when the precursor was heated at 200° C., —O— absorption (1,166 $cm^{-1}$) was disappeared, and C=O absorption was shifted from 1,730 $cm^{-1}$ to 1,707 $cm^{-1}$. This shows that 2-butyloctanoic acid was separated from the precursor molecule.

Moreover, it was observed that when the precursor was heated at 330° C., C=O absorption derived from 2-butyloctanoic acid (1,707 $cm^{-1}$) was disappeared, and the spectrum had only peaks derived from aromatic series and olefin.

Figure 2:
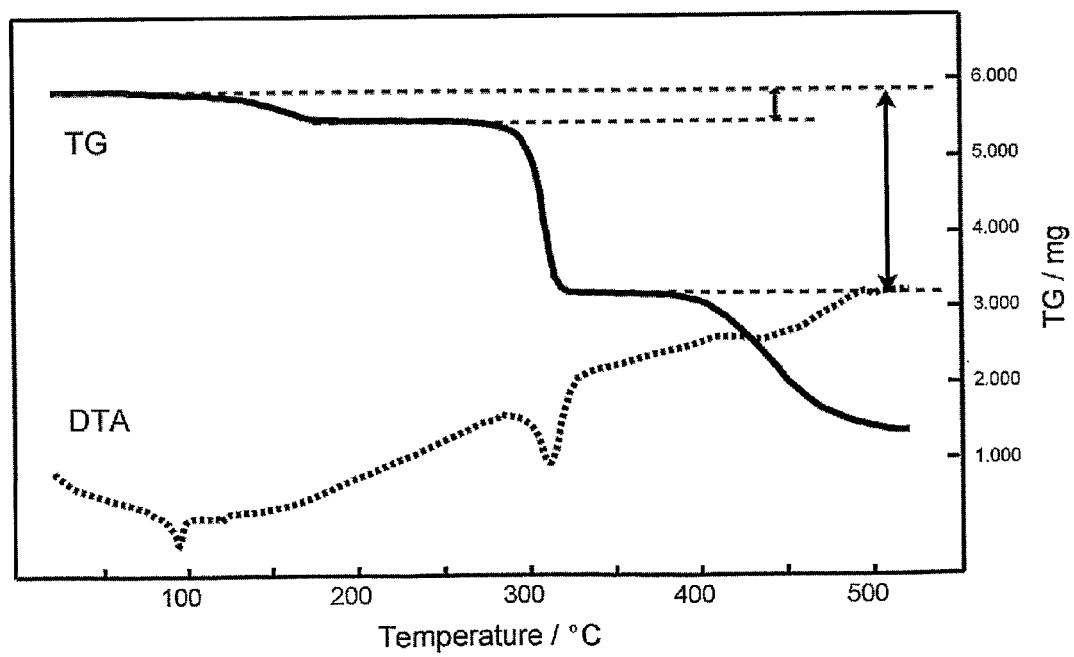
FIG. 2 shows TG-DTA data of Precursor 1 of the present invention.

The pyrolysis behavior of Precursor 1 was observed by TG-DTA (manufactured by Seiko Instruments Inc.) using 5 mg of a sample and 5 mg of $Al_2O_3$ as a reference in a nitrogen atmosphere. The results are shown in FIG. 2.

Upon heating at 290° C. to 330° C., a mass decrease corresponding to 2 molecules of 2-butyloctanoic acid could be observed. Thus, transformation from Precursor 1 to Specific Compound OSC 1 was confirmed.

Example 12

Observation of Elimination Behavior of Precursor Synthesized in Example 2

Precursor 2 synthesized in Example 2 (5 mg) was heated on a silicon wafer which was placed on a hot plate set at given temperatures of 150° C., 160° C., 170° C., 180° C., 200° C., 220° C., 270° C. and 330° C. for 30 minutes so as to prepare a sample. IR spectra (KBr method, SPECTRUM GX FT-IR SYSTEM manufactured by PerkinElmer, Inc.) of the sample, a precursor before heating and 2-butyloctanoic acid produced by elimination reaction were measured. The results are shown in FIG. 3.

Figure 3:
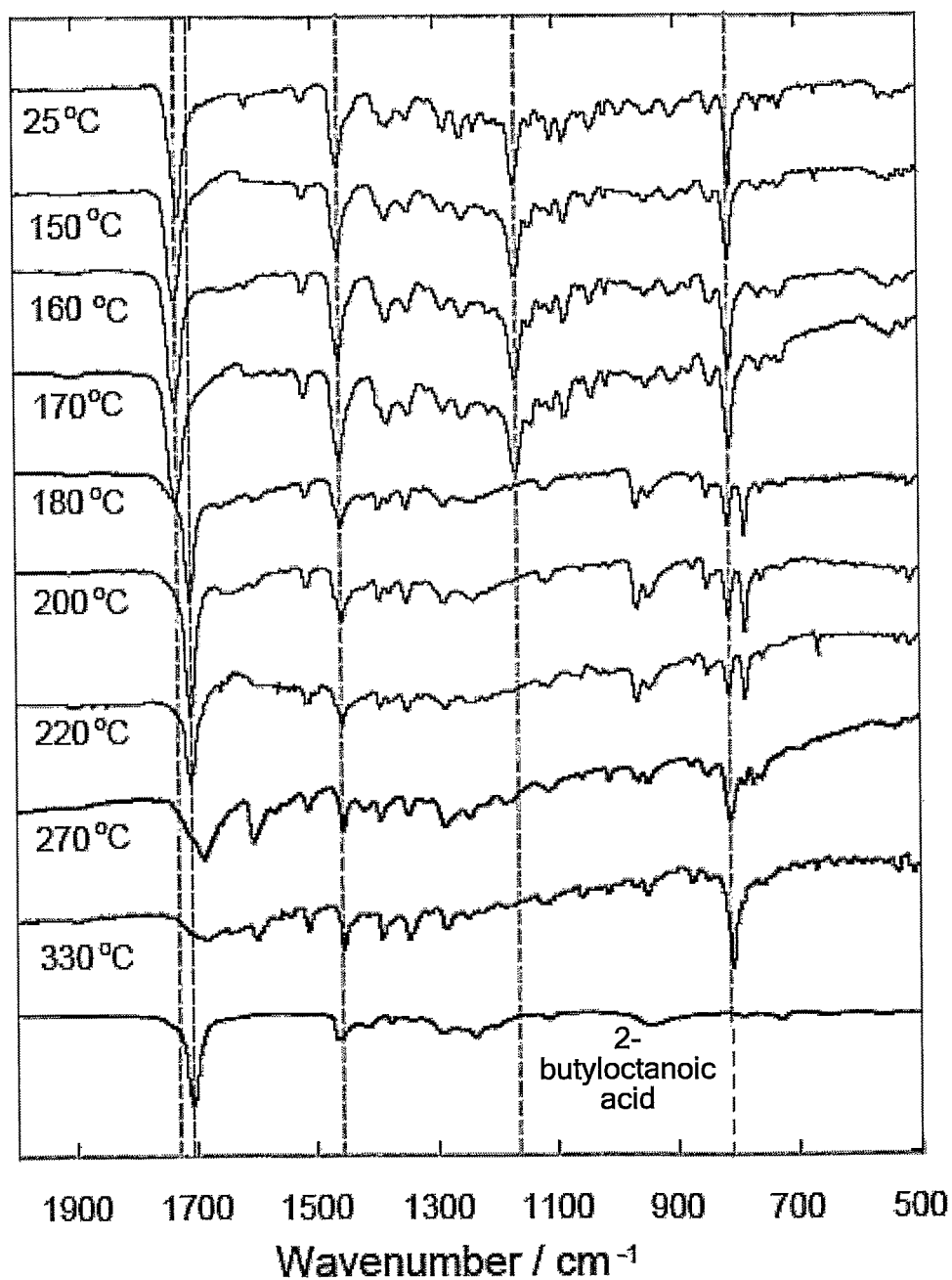
FIG. 3 shows IR spectra of Precursor 2 of the present invention (temperature variation from a room temperature to 330° C.) and an IR spectrum of a separated carboxylic acid.

In FIG. 3, a threshold occurred at 180° C., —O— absorption (1,166 $cm^{-1}$) was disappeared, and C=O absorption was shifted from 1,730 $cm^{-1}$ to 1,707 $cm^{-1}$. Thus, a temperature where 2-butyloctanoic acid was separated from a precursor molecule could be found, which had been hard to be estimated only from the amount of mass decrease measured by TG-DTA.

Moreover, two peaks (cis conformation and trans conformation) of a terminal olefin existing around 800 $cm^{-1}$ could be observed.

When the sample was heated at 330° C., C=O absorption derived from 2-butyloctanoic acid (1,707 $cm^{-1}$) was disappeared, and the spectrum had one peak of olefin. Thus, transformation from Precursor 2 to Specific Compound OSC 2 was confirmed.

Example 13

Film Deposition of Precursor 1 Synthesized in Example 1

Precursor 1 synthesized in Example 1 was dissolved respectively in chloroform, toluene and THF so as to be contained therein in concentrations of 1.0% by mass and 5.0% by mass, and then passed through a filter so as to prepare each solution. The solution was left to stand over night at a room temperature, and solute separation was not observed at all in any solvent and concentration.

Next, film was deposited on a silicon substrate using each solution by spin coating in a rotational condition of 500 rpm for 5 seconds and additionally 3,000 rpm for 30 seconds.

By using any solution, a smooth and homogeneous continuous film could be obtained. The film was observed under a light microscope and contact mode AFM (manufactured by Seiko Instruments Inc.).

A solvent resistance test was performed in such a manner that a deposited film was annealed on a hot plate at 200° C. in an atmosphere for 30 minutes, and reciprocally rubbed once with BEMCOT M-3 (manufactured by ASAHI KASEI FIBERS CORPORATION) which was impregnated with chloroform, toluene or THF, and then the state of the film was observed. The film was not dissolved or peeled by using any of the solvents, and kept the state at the time of film deposition.

Figure 4A:
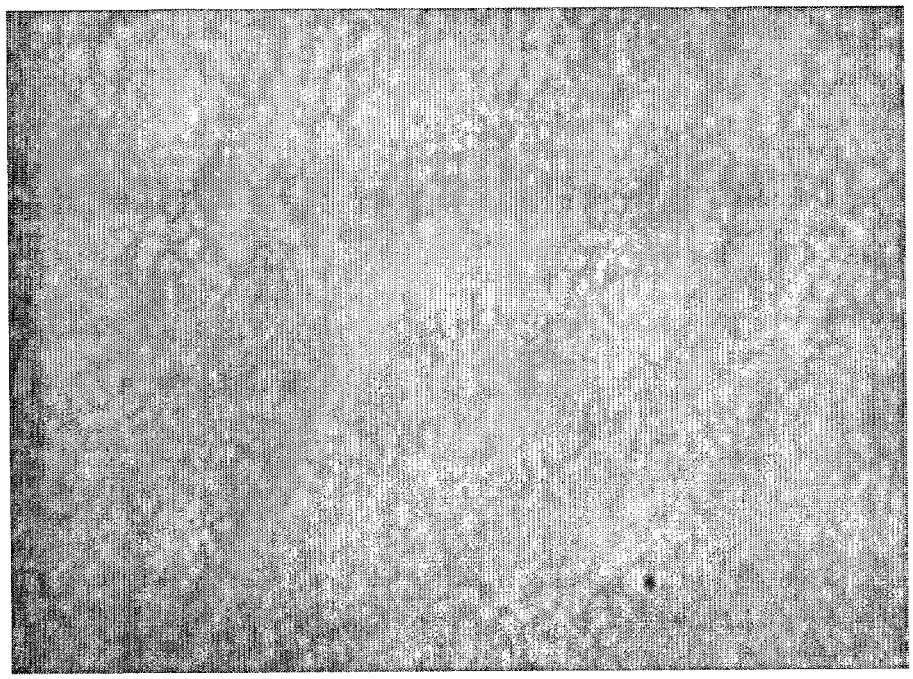
FIG. 4A is an example of a polarization microscopic image (crossed Nichol) of a precursor film of the present invention before annealing (magnification: 400×).
Figure 4B:
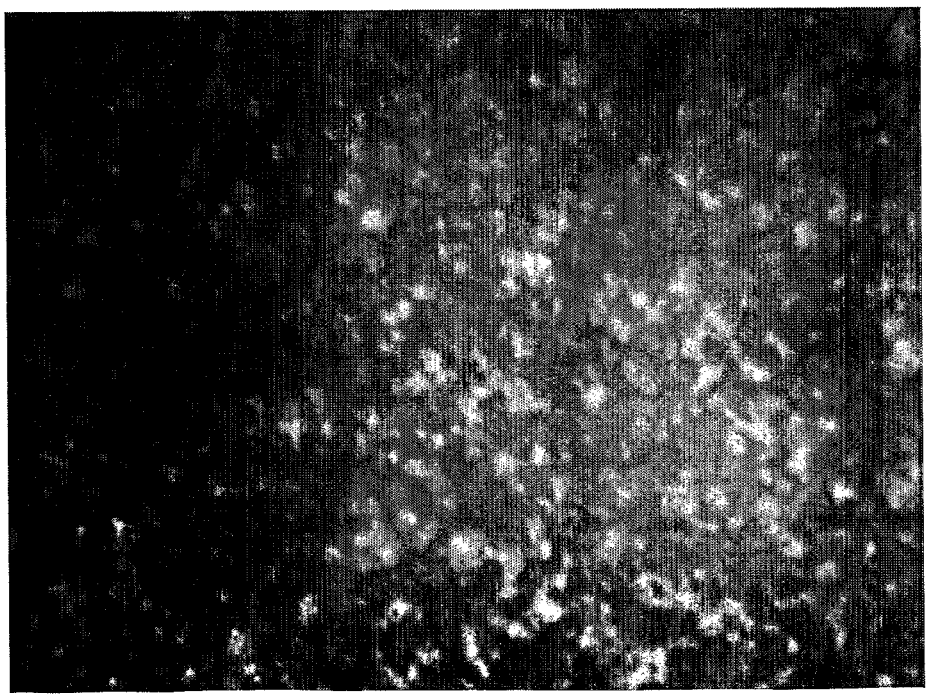
FIG. 4B is an example of a polarization microscopic image (crossed Nichol) of a precursor film of the present invention after annealing at 200° C. (magnification: 400×).

Moreover, polarization microscopic images before and after annealing treatment are shown in FIGS. 4A and 4B. The image before annealing treatment was dark all over and a film was isotropic. Consequently, it was found that the film before annealing treatment was amorphous.

On the other hand, a plurality of colored domains were observed in the image after annealing treatment. Consequently, it was found that the film after annealing treatment was crystalline. This was because a precursor eliminated a soluble group so as to be transformed into the specific compound of the present invention, which was crystalline.

Example 14

Film Deposition of Precursor 2 Synthesized in Example 2

A solution preparation, film deposition and solvent resistance test of the film were performed in the same manner as in Example 13, except that Precursor 1 in Example 13 was changed to Precursor 2 synthesized in Example 2.

Example 15

Film Deposition of Precursor 3 Synthesized in Example 3

A solution preparation, film deposition and solvent resistance test of the film were preformed in the same manner as in Example 13, except that Precursor 1 in Example 13 was changed to Precursor 3 synthesized in Example 3.

Example 16

Film Deposition of Precursor 4 Synthesized in Example 4

A solution preparation, film deposition and solvent resistance test of the film were preformed in the same manner as in Example 13, except that Precursor 1 in Example 13 was changed to Precursor 4 synthesized in Example 4.

Comparative Example 1

A solution preparation, film deposition and solvent resistance test of the film were preformed in the same manner as in Example 13, except that Precursor 1 in Example 13 was changed to 2,7-diphenyl [1]benzothieno[3,2-b][1]benzothiophene.

Comparative Example 2

A solution preparation, film deposition and solvent resistance test of the film were preformed in the same manner as in Example 13, except that Precursor 1 in Example 13 was changed to 2,7-dioctyl[1]benzothieno[3,2-b][1]benzothiophene.

The results of Examples 13 to 16 and Comparative Examples 1 and 2 are shown in Table 1.

TABLE 1

|  | Solubility | Film deposition | Solvent resistance of film after heating |
|---|---|---|---|
| Example 13 | A | A | A |
| Example 14 | A | A | A |
| Example 15 | A | A | A |
| Example 16 | A | A | A |
| Comparative Example 1 | C | B | B |
| Comparative Example 2 | B | A | C |

The evaluation criteria of the solubility in Table 1 are as follows:

A: No precipitation of a solute was observed when a precursor was dissolved in each solution so as to be contained in a concentration of 5% by mass, and then left to stand for 12 hours at a room temperature.

B: No precipitation of a solute was observed when a precursor was dissolved in each solution so as to be contained in a concentration of 1% by mass, and then left to stand for 12 hours at a room temperature.

C: Precipitation of a solute was observed when a precursor was dissolved in each solution so as to be contained in a concentration of 1% by mass, and then left to stand for 12 hours at a room temperature.

The evaluation criteria of the film deposition in Table 1 are as follows:

A: A continuous film was obtained.

B: A non-continuous film was obtained.

The evaluation criteria of the solvent resistance of film in Table 1 are as follows:

A: A film was not dissolved in a solvent used for film deposition and no peeling occurred.

B: A film was dissolved in a solvent used for film deposition or peeling occurred.

C: A film was dissolved in a solvent used for film deposition and peeling occurred.

As can be seen from the results of Table 1, the precursor of the present invention had a high solubility to a general organic solvent and film deposition property in which a film was not influenced by a solvent, and was heated to eliminate a soluble group so as to transform an amorphous film to a crystalline film of the specific compound. Moreover, the film containing the specific compound of the present invention, which had been transformed from the precursor, had high crystallinity and exhibited high solvent resistance.

Example 17

Production and Evaluation of Field-Effect Transistor by Vacuum Process

Figure 5A:
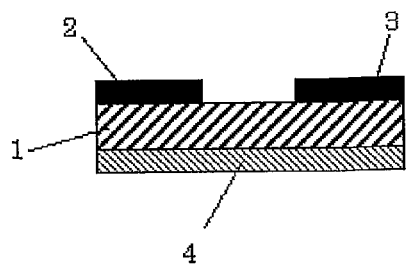
FIG. 5A shows a schematic view of an example of an organic thin-film transistor of the present invention (first).
Figure 5B:
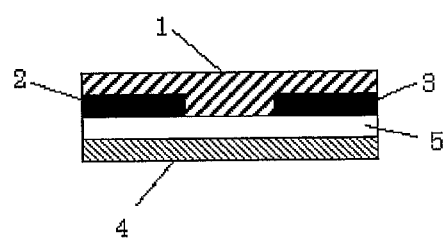
FIG. 5B shows a schematic view of the example of an organic thin-film transistor of the present invention (second).
Figure 5C:
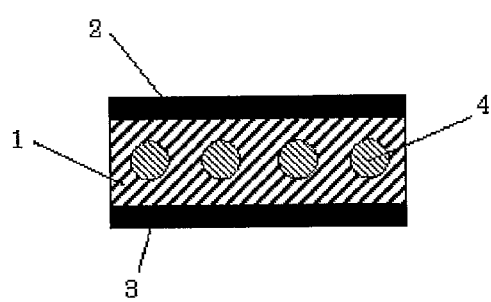
FIG. 5C shows a schematic view of the example of an organic thin-film transistor of the present invention (third).
Figure 5D:
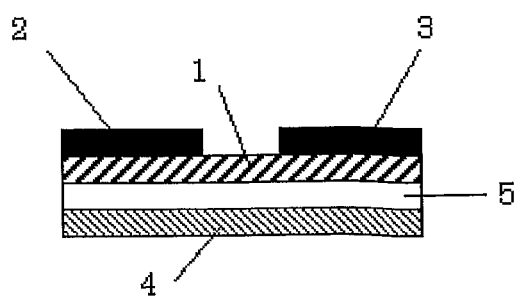
FIG. 5D shows a schematic view of the example of an organic thin-film transistor of the present invention (fourth).

By using Specific Compound OSC 1 synthesized in Example 5, a field-effect transistor having a configuration of FIG. 5D was produced in the following manner.

A N-type silicon substrate including a thermally-oxidized film having a film thickness of 300 nm was immersed and washed in a concentrated sulfuric acid for 24 hours, and then immersed in a toluene solution of phenyltrichlorosilane (concentration: 1 mM, fluid volume: 8 mL) in a vessel. The vessel was sealed and irradiated with ultrasonic wave for 30 minutes, and then the substrate was subjected to ultrasonic cleaning using toluene and acetone so as to treat a surface of a silicon oxide film, thereby forming a monomolecular film.

On the thus prepared substrate Specific Compound OSC 1 synthesized in Example 5 was vacuum deposited under the condition of back pressure of up to $10^{-4}$ Pa, deposition rate of 1 Å/s to 2 Å/s and semiconductor film thickness of 60 nm, thereby depositing an organic semiconductor film.

On the organic semiconductor film gold was vapor deposited via a shadow mask under the condition of back pressure of up to $10^{-4}$ Pa, deposition rate of 1 Å/s to 2 Å/s and film thickness of 50 nm, thereby forming source and drain electrodes having a channel length of 50 μm and channel width of 2 mm. The organic semiconductor film and silicon oxide film in a region other than the electrodes was removed by scraping, and a conductive paste (manufactured by Fujikura Kasei Co., Ltd.) was applied in the region and a solvent therein was dried. Through the region, voltage was applied to the silicon substrate serving as the gate electrode, thereby producing a field-effect transistor (FET) element.

Figure 6:
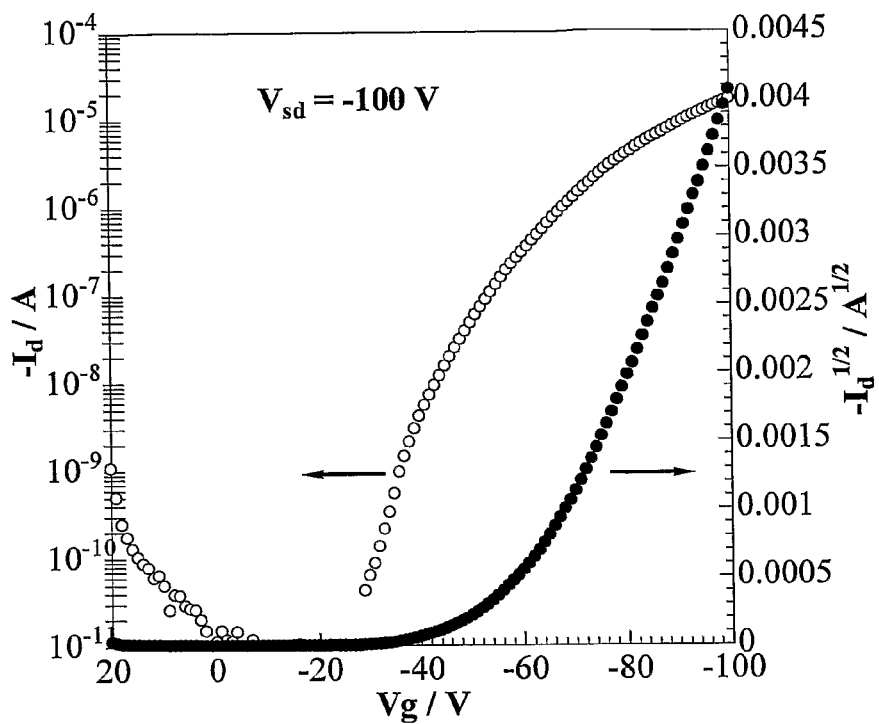
FIG. 6 shows an I-V transfer characteristics of an organic thin-film transistor of the present invention produced by a vacuum process.

The electric property of the FET element was evaluated by a semiconductor parameter analyzer 4156C (manufactured by Agilent Technologies). The FET element exhibited a property as a p-type transistor element. The current and voltage (I-V) characteristics of an organic thin film transistor is shown in FIG. 6. From the saturation region, a field-effect mobility was obtained.

The field-effect mobility of the organic thin-film transistor was calculated by the following equation.

$$Ids = \mu C_{in} W (Vg-Vth)^2/2L$$

In the equation, Cin is a capacitance per unit area of a gate insulating film, W is a channel width, L is a channel length, Vg is a gate voltage, Ids is a source-chain current, μ is a field effect mobility and Vth is a gate threshold voltage at which a channel begins to be formed.

In FIG. 6, a white circle represents an absolute value of drain current, and a black circle represents a square root of the absolute value of drain current (Example 17).

Example 18

Production and Evaluation of Field-Effect Transistor by Vacuum Process

A field-effect transistor element was produced and an electric property thereof was evaluated in the same manner as in Example 17, except that Specific Compound OSC 1 of Example 17 was changed to Specific Compound OSC 2 synthesized in Example 6.

As a result, the field-effect transistor element exhibited a property as a p-type transistor element similar to that in Example 17.

Figure 8:
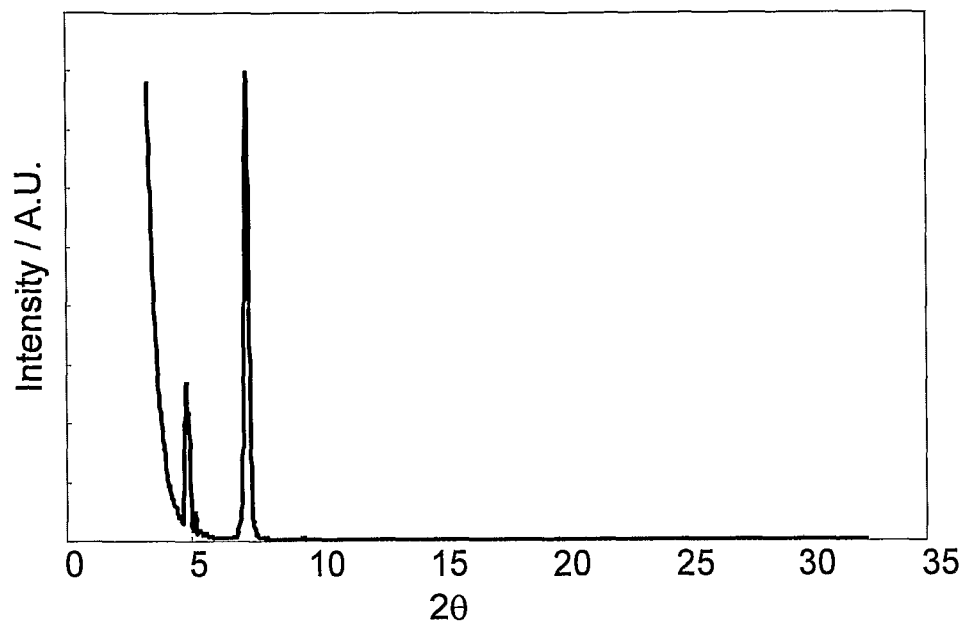
FIG. 8 shows an out-of-plane X ray diffraction pattern of the deposited film of Specific Compound OSC 2 of the present invention produced in Example 18.
Figure 9:
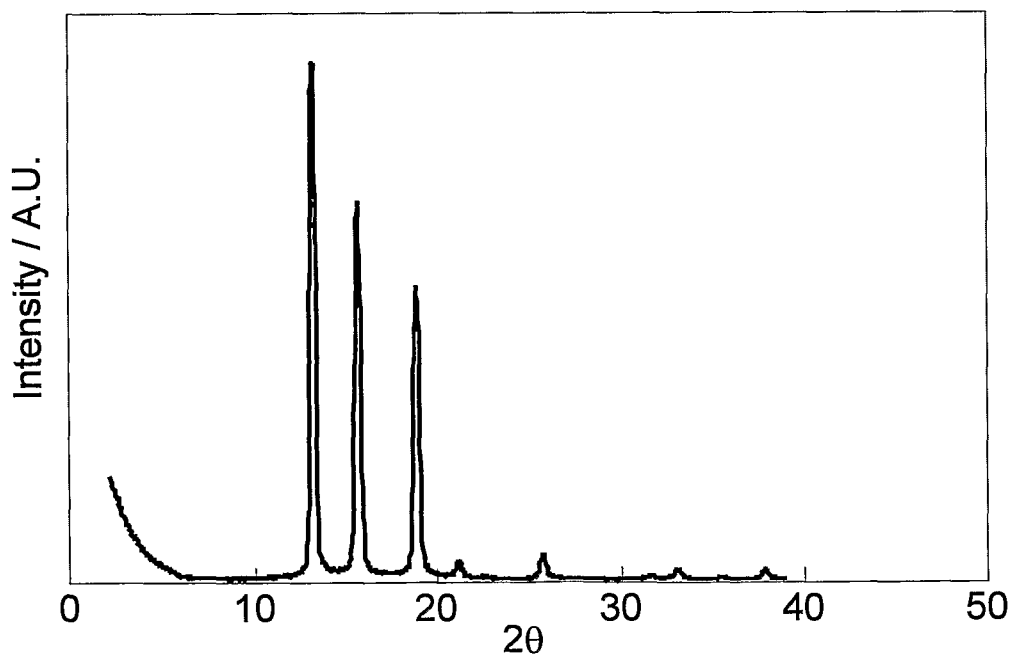
FIG. 9 shows an in-plane X ray diffraction pattern of the deposited film of Specific Compound OSC 2 of the present invention produced in Example 18.

The in-plane and out-of-plane X ray diffraction patterns of the deposited film of the produced compound are shown in FIGS. 8 and 9.

Example 19

Production and Evaluation of Field-Effect Transistor by Vacuum Process

A field-effect transistor element was produced and an electric property thereof was evaluated in the same manner as in Example 17, except that Specific Compound OSC 1 of Example 17 was changed to Specific Compound OSC 3 synthesized in Example 7.

As a result, the field-effect transistor element exhibited a property as a p-type transistor element similar to that in Example 17.

Example 20

Production and Evaluation of Field-Effect Transistor by Vacuum Process

A field-effect transistor element was produced and an electric property thereof was evaluated in the same manner as in Example 17, except that Specific Compound OSC 1 of Example 17 was changed to Specific Compound OSC 4 synthesized in Example 8.

As a result, the field-effect transistor element exhibited a property as a p-type transistor element similar to that in Example 17.

Example 21

Production and Evaluation of Field-Effect Transistor by Vacuum Process

A field-effect transistor element was produced and an electric property thereof was evaluated in the same manner as in Example 17, except that Specific Compound OSC 1 of Example 17 was changed to Specific Compound OSC 5 synthesized in Example 9.

As a result, the field-effect transistor element exhibited a property as a p-type transistor element similar to that in Example 17.

The current on/off ratios and field effect mobilities (as a carrier mobility, not an electron mobility, but a hole mobility in particular) of Examples 17 to 21 are shown in Table 2.

TABLE 2

|  | hole mobility ($cm^2/Vs$) | on/off ratio |
| --- | --- | --- |
| Example 17 | $1.7 \times 10^{-1}$ | $2.6 \times 10^7$ |
| Example 18 | $1.8 \times 10^{-1}$ | $4.2 \times 10^7$ |
| Example 19 | $1.1 \times 10^{-1}$ | $3.3 \times 10^6$ |
| Example 20 | $6.2 \times 10^{-3}$ | $6.2 \times 10^4$ |
| Example 21 | $4.8 \times 10^{-2}$ | $6.2 \times 10^5$ |

Example 22

Production and Evaluation of Field-Effect Transistor by Solution Process

By using Precursor 1 synthesized in Example 1, a field-effect transistor having a configuration of FIG. 5D was produced in the following manner.

On the silicon substrate on which a monomolecular film had been formed by the method described in Example 17, a chloroform solution of Precursor 1 (0.2% by mass) was dripped. Thereafter, the chloroform was evaporated so as to deposit a 100 nm-thick continuous precursor film. By heating the substrate on a hot plate at 200° C., the precursor film was transformed to an organic semiconductor film.

On the organic semiconductor film gold was vapor deposited via a shadow mask under the condition of back pressure of up to $10^{-4}$ Pa, deposition rate of 1 Å/s to 2 Å/s and film thickness of 50 nm, thereby forming source and drain electrodes having a channel length of 50 μm and channel width of 2 mm. The organic semiconductor film and silicon oxide film in a region other than the electrodes was removed by scraping, and a conductive paste (manufactured by Fujikura Kasei Co., Ltd.) was applied in the region and the solvent was dried. Through the region, voltage was applied to the silicon substrate serving as the gate electrode, thereby producing a field-effect transistor (FET) element.

Figure 7:
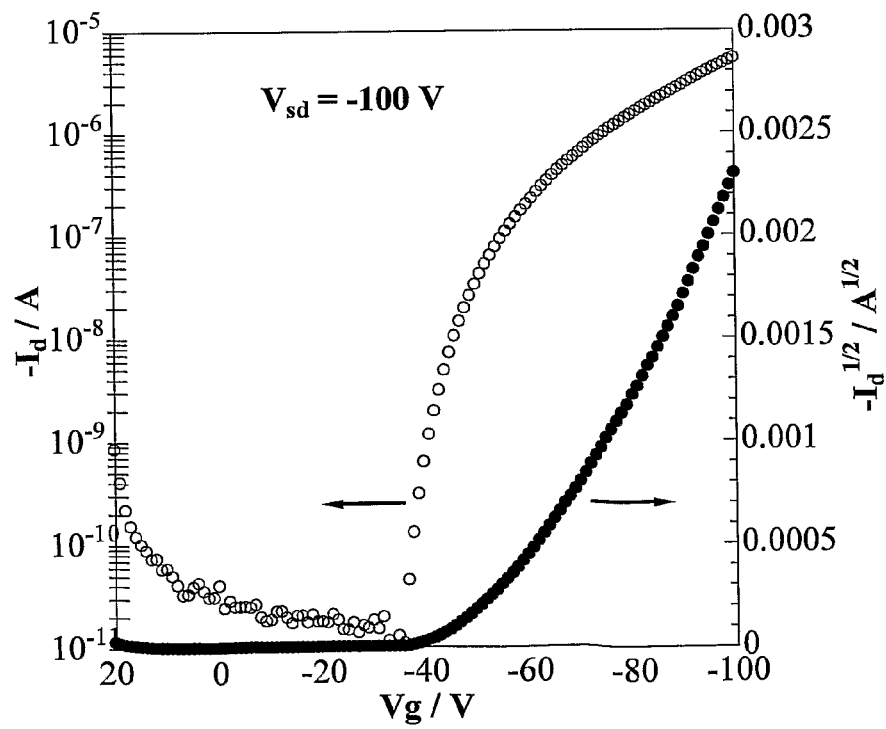
FIG. 7 shows an I-V transfer characteristics of an organic thin-film transistor of the present invention produced by a solution process.

The electric property of the FET element was evaluated by a semiconductor parameter analyzer 4156C (manufactured by Agilent Technologies). The FET element exhibited a property as a p-type transistor element. The current and voltage (I-V) characteristics of an organic thin film transistor is shown in FIG. 7. From the saturation region, a field-effect mobility was obtained.

The field-effect mobility of the organic thin-film transistor was calculated by the following equation.

$$Ids = \mu Cin W(Vg-Vth)^2/2L$$

In the equation, Cin is a capacitance per unit area of a gate insulating film, W is a channel width, L is a channel length, Vg is a gate voltage, Ids is a source-drain current, μ is a field effect mobility and Vth is a gate threshold voltage at which a channel begins to be formed.

In FIG. 7, a white circle represents an absolute value of drain current, and a black circle represents a square root of the absolute value of drain current (Example 22).

Example 23

Production and Evaluation of Field-Effect Transistor by Solution Process

A field-effect transistor element was produced and an electric property thereof was evaluated in the same manner as in Example 22, except that Precursor 1 of Example 22 was changed to Precursor 2 synthesized in Example 2.

As a result, the field-effect transistor element exhibited a property as a p-type transistor element similar to that in Example 22.

Example 24

Production and Evaluation of Field-Effect Transistor by Solution Process

A field-effect transistor element was produced and an electric property thereof was evaluated in the same manner as in Example 22, except that Precursor 1 of Example 22 was changed to Precursor 3 synthesized in Example 3.

As a result, the field-effect transistor element exhibited a property as a p-type transistor element similar to that in Example 22.

Example 25

Production and Evaluation of Field-Effect Transistor by Solution Process

A field-effect transistor element was produced and an electric property thereof was evaluated in the same manner as in Example 22, except that Precursor 1 of Example 22 was changed to Precursor 4 synthesized in Example 4.

As a result, the field-effect transistor element exhibited a property as a p-type transistor element similar to that in Example 22.

The current on/off ratios and field effect mobilities (as a carrier mobility, not an electron mobility, but a hole mobility in particular) of Examples 22 to 25 are shown in Table 3.
Property of Field-Effect Transistor Produced by Solution Process

TABLE 3

| | hole mobility (cm$^2$/Vs) | on/off ratio |
|---|---|---|
| Example 22 | $4.8 \times 10^{-2}$ | $2.7 \times 10^5$ |
| Example 23 | $5.2 \times 10^{-2}$ | $5.2 \times 10^5$ |
| Example 24 | $3.7 \times 10^{-2}$ | $2.3 \times 10^5$ |
| Example 25 | $4.3 \times 10^{-2}$ | $3.3 \times 10^5$ |

As is clear from Tables 1 and 2, the field-effect transistor of the present invention produced by vacuum deposition process or solution process had excellent properties as an organic transistor, because it had high field-effect mobility and current on/off ratio.

Industrial Applicability

The specific compound of the present invention can be synthesized from a precursor having excellent solubility to various organic solvents by elimination reaction occurred by application of energy, thereby having excellent processability. As the specific compound is insoluble to an organic solvent after elimination reaction, the compound and precursor thereof may be applied to organic electronic devices, particularly, applied to electronic devices such as semiconductors, and optical electronic devices such as EL light-emitting elements.

As the organic transistor using the compound of the present invention has high field-effect mobility and current on/off ratio, it may be possibly applied to liquid crystal display elements, EL light-emitting elements, electronic paper, various sensors, and radio frequency identifications (RFIDs).

The invention claimed is:

1. A [1]benzothieno[3,2-b][1]benzothiophene compound represented by formula (I):

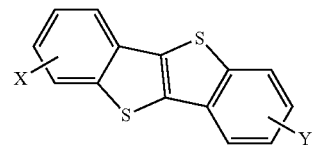

Formula (I)

wherein X and Y are each independently a hydrogen atom, a halogen atom, a functional group which is a straight or branched aliphatic alkenyl group or an alicyclic alkenyl group which is represented by formula (II), a functional group having a carboxyl group which is represented by formula (III), and a functional group having a thiol group which is represented by formula (IV):

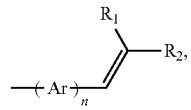

Formula (II)

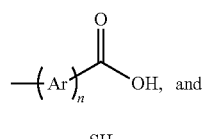

Formula (III)

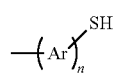

Formula (IV)

wherein Ar is selected from the group consisting of optionally substituted benzene, optionally substituted thiophene, optionally substituted naphthalene and optionally substituted thienothiophene, n is an integer of 1 or more, when n is 2 or more, the plurality of Ar groups are the same or each independently different, $R_1$ and $R_2$ are each independently a hydrogen atom, a straight or branched aliphatic alkyl group optionally having a halogen atom, or an alicyclic alkyl group optionally having a halogen atom;

provided that at least one of X and Y is the functional group of formula (II), the functional group of formula (III) or the functional group of formula (IV).

2. The [1]benzothieno[3,2-b][1]benzothiophene compound according to claim 1, wherein n is 1 or 2.

3. A method for producing the [1]benzothieno[3,2-b][1]benzothiophene compound according to claim 1, comprising:

transforming a [1]benzothieno[3,2-b][1]benzothiophene compound precursor comprising a structure of formula (V) into the [1]benzothieno[3,2-b][1]benzothiophene compound of formula (I) wherein at least one of X and Y is the functional group of formula (II);

transforming a [1]benzothieno[3,2-b][1]benzothiophene compound precursor comprising a structure of formula (VI) into the [1]benzothieno[3,2-b][1]benzothiophene compound of formula (I) wherein at least one of X and Y is the functional group of formula (III); or transforming a [1]benzothieno[3,2-b][1]benzothiophene compound precursor comprising a structure of formula (VII) into the [1]benzothieno[3,2-b][1]benzothiophene compound of formula (I) wherein at least one of X and Y is the functional group of formula (IV):

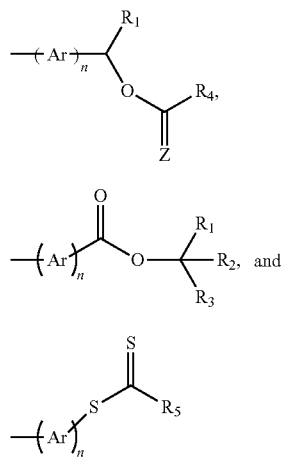

Formula (V)

Formula (VI)

Formula (VII)

wherein, in Formulas (V) to (VII), n is an integer of 1 or more, Ar is selected from the group consisting of optionally substituted benzene, optionally substituted thiophene, optionally substituted naphthalene and optionally substituted thienothiophene, when n is an integer of 2 or more, the plurality of Ar groups are the same or each independently different, Z is an oxygen atom or a sulfur atom, $R_1$, $R_2$ and $R_3$ are each independently a hydrogen atom, a straight or branched aliphatic alkyl group optionally having a halogen atom or an alicyclic alkyl group optionally having a halogen atom, $R_4$ is a hydrogen atom, an aliphatic alkyl group having 1 or more carbon atoms and optionally having a halogen atom, an alicyclic alkyl group having 1 or more carbon atoms and optionally having a halogen atom, and a straight or branched alkoxyl group having 1 or more carbon atoms and optionally having a halogen atom, a straight or branched thioalkoxyl group having 1 or more carbon atoms and optionally having a halogen atom, and $R_5$ is a straight or branched alkoxyl group having 1 or more carbon atoms.

4. An organic electronic device comprising the [1]benzothieno[3,2-b][1]benzothiophene compound according to claim 1.

5. The organic electronic device according to claim 4, wherein the organic electronic device comprises the [1]benzothieno[3,2-b][1]benzothiophene compound produced by a method for producing the [1]benzothieno[3,2-b][1]benzothiophene compound, which comprises:

transforming a [1]benzothieno[3,2-b][1]benzothiophene compound precursor comprising a structure of formula (V) into the [1]benzothieno[3,2-b][1]benzothiophene compound of formula (I) wherein at least one of X and Y is the functional group of formula (II);

transforming a [1]benzothieno[3,2-b][1]benzothiophene compound precursor comprising a structure of formula (VI) into the [1]benzothieno[3,2-b][1]benzothiophene compound of formula (I) wherein at least one of X and Y is the functional group of formula (III); or transforming a [1]benzothieno[3,2-b][1]benzothiophene compound precursor comprising a structure of formula (VII) into the [1]benzothieno[3,2-b][1]benzothiophene compound of formula (I) wherein at least one of X and Y is the functional group of formula (IV):

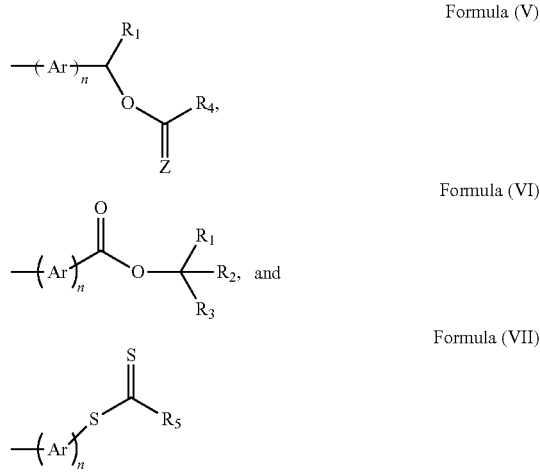

Formula (V)

Formula (VI)

Formula (VII)

wherein, in formulas (V), (VI) and (VII), n is an integer of 1 or more; Ar is selected from the group consisting of optionally substituted benzene, optionally substituted thiophene, optionally substituted naphthalene and optionally substituted thienothiophene; when n is an integer of 2 or more, the plurality of Ar groups are the same or each independently different; Z is an oxygen atom or a sulfur atom; $R_1$, $R_2$ and $R_3$ are each independently a hydrogen atom, a straight or branched aliphatic alkyl group optionally having a halogen atom or an alicyclic alkyl group optionally having a halogen atom; $R_4$ is a hydrogen atom, an aliphatic alkyl group having 1 or more carbon atoms and optionally having a halogen atom, an alicyclic alkyl group having 1 or more carbon atoms and optionally having a halogen atom, and a straight or branched alkoxyl group having 1 or more carbon atoms and optionally having a halogen atom, a straight or branched thioalkoxyl group having 1 or more carbon atoms and optionally having a halogen atom; and $R_5$ is a straight or branched alkoxyl group having 1 or more carbon atoms.

6. The organic electronic device according to claim 4, wherein the organic electronic device is an organic thin-film transistor.

* * * * *